US010675211B2

(12) United States Patent
Nakanishi

(10) Patent No.: US 10,675,211 B2
(45) Date of Patent: Jun. 9, 2020

(54) COSMETIC DEVICE

(71) Applicant: UNISH INC., Osaka-shi, Osaka (JP)

(72) Inventor: Hirofumi Nakanishi, Osaka (JP)

(73) Assignee: UNISH INC., Osaka-Shi (JP)

( * ) Notice: Subject to any disclaimer, the term of this patent is extended or adjusted under 35 U.S.C. 154(b) by 365 days.

(21) Appl. No.: 15/579,812

(22) PCT Filed: Aug. 30, 2016

(86) PCT No.: PCT/JP2016/075343
§ 371 (c)(1),
(2) Date: Dec. 5, 2017

(87) PCT Pub. No.: WO2017/038822
PCT Pub. Date: Mar. 9, 2017

(65) Prior Publication Data
US 2018/0161233 A1    Jun. 14, 2018

(30) Foreign Application Priority Data

Aug. 31, 2015 (JP) .................................. 2015-171215

(51) Int. Cl.
*A61H 15/00* (2006.01)
*A61H 7/00* (2006.01)
(Continued)

(52) U.S. Cl.
CPC ........... *A61H 15/0085* (2013.01); *A61H 7/00* (2013.01); *A61H 7/003* (2013.01); *A61H 7/005* (2013.01);
(Continued)

(58) Field of Classification Search
CPC ............ A61H 15/0085; A61H 15/0092; A61H 2207/00; A61H 7/00; A61H 7/002;
(Continued)

(56) References Cited

U.S. PATENT DOCUMENTS 5,797,966 A * 8/1998 Bontoux ................ A61H 7/008
601/125
5,885,232 A * 3/1999 Guitay ................... A61H 7/008
601/6
(Continued)

FOREIGN PATENT DOCUMENTS

JP    2002-527202 A    8/2002
JP    2003-534875 A    11/2003
(Continued)

OTHER PUBLICATIONS

ISA/JP, International Search Report dated Oct. 4, 2017 in International Application No. PCT/JP2016/075343, a total of 4 pages with English translation.
(Continued)

*Primary Examiner* — Bradley H Philips
*Assistant Examiner* — Vincent D Hoang
(74) *Attorney, Agent, or Firm* — Masuvalley & Partners

(57) ABSTRACT

The present invention provides a cosmetic device having a massage function by rolling a roller disposed to a main body part, a suction function with a suction unit, and a stimulation function by outputting a stimulation signal with the roller. Since these functions can be combined and performed in use, the cosmetic device can synergistically exert an effect of dissolving cellulite of user's skin and releasing fascia. While the cosmetic device is multi-functional, the main body part has a compact structure with the suction unit inside and the roller on a bottom surface that are arranged and integrated, as well as an insertion part formed by a space that can be inserted with a user's hand, and a placement part that can be placed with a palm of the user's hand inserted into the insertion part, allowing the cosmetic device to be easily used by holding with one hand.

10 Claims, 13 Drawing Sheets

(51) Int. Cl.
*A61N 1/32* (2006.01)
*A61H 23/02* (2006.01)

(52) U.S. Cl.
CPC ......... *A61H 15/00* (2013.01); *A61H 15/0092* (2013.01); *A61H 23/02* (2013.01); *A61H 23/0245* (2013.01); *A61N 1/322* (2013.01); *A61H 2015/0014* (2013.01); *A61H 2201/10* (2013.01); *A61H 2207/00* (2013.01)

(58) Field of Classification Search
CPC .... A61H 7/003; A61H 7/005; A61H 2201/10; A61H 23/0345; A61H 23/02; A61N 1/322; A41D 19/0013; A41D 19/0017; A41D 19/0024; A41D 19/0027; A41D 19/0031
See application file for complete search history.

(56) References Cited

U.S. PATENT DOCUMENTS

| | | | | |
|---|---|---|---|---|
| 5,891,064 | A * | 4/1999 | Van Herk | A61H 7/008 601/122 |
| 6,585,667 | B1 * | 7/2003 | Muller | A61H 7/008 601/6 |
| 8,348,866 | B2 * | 1/2013 | Tudico | A61H 15/0085 601/7 |
| 2005/0119594 | A1 * | 6/2005 | Piana | A61H 7/008 601/7 |
| 2008/0221504 | A1 * | 9/2008 | Aghion | A61H 7/008 604/20 |

FOREIGN PATENT DOCUMENTS

| | | |
|---|---|---|
| JP | 2004-243056 A | 9/2004 |
| JP | 2005-058593 A | 3/2005 |
| JP | 2011-045610 A | 3/2011 |
| JP | 2013-094176 A | 5/2013 |

OTHER PUBLICATIONS

IPEA/JP, International Preliminary Report on Patentability dated Jun. 13, 2017 for International Patent Application No. PCT/JP2016/075343, 11 pages with English translation.

* cited by examiner

BEFORE TREATMENT

AFTER TREATMENT

BEFORE TREATMENT

AFTER TREATMENT

COSMETIC DEVICE

RELATED APPLICATIONS

This application is the U.S. National Phase application under 35 U.S.C. § 371 of International Patent Application No. PCT/JP2016/075343, international filing date Aug. 30, 2016, entitled "COSMETIC DEVICE"; which claims priority to Japanese Patent Application No. 2015-171215 filed on Aug. 31, 2015, which are hereby expressly incorporated by reference in their entireties for all purposes.

BACKGROUND

Technical Field

The present invention relates to a cosmetic device. More particularly, the present invention relates to a cosmetic device that serves to dissolve cellulite and the like.

Related Art

In general, cellulite is said to indicate tissue and the like, in the subcutaneous tissue, that exists in a nonuniform or block shape mainly in the abdomen, buttocks, and thighs, and has grown large as fat cells adjacent to blood vessels are separated and float away from the blood vessels, and the fat cells are adhered with waste products, moisture, and the like, and entangled with collagen or the like. In a human being, swelling or hypertrophy of fat and the like compresses nerves, blood vessels, and the like, and causes excessive components and waste products to adhere around fat cells, interfering with metabolism of fat. For example, sitting in a chair for a long time also causes weight to be applied to back thighs, the buttocks, and the like to induce blood circulation disturbance, causing cellulite to be easily generated.

In addition, cellulite is particularly prone to be formed in a woman's body, and it is generally said that cellulite exists in 80 to 90% or more of women. On the other hand, cellulite has a nature that it is difficult to be dissolved by exercise or dietary restrictions alone, once being formed. Therefore, in order to eliminate obesity, special treatment and operation aimed at dissolving cellulite are required.

In recent years, various cosmetic devices intended for cosmetic effects have been studied. Here, it is known that a massage effect can be provided by rotating and rolling a rotatable roller while being placed on the skin, cutis, or the like (hereinafter may also be simply referred to as "skin or the like"). Further, a cosmetic device using such a roller is provided, and a cosmetic device using an eccentric roller or vibrating a roller is also known (e.g., see JP 2004-243056 A). There is also provided a cosmetic device including a suction unit or a decompression unit such as a pump, and utilizing a suction function or the like (see, e.g., JP 2005-58593 A).

SUMMARY

However, in practice, rolling a roller alone provides massage simply on skin or the like, and there are many cases where it is not very useful for dissolving cellulite and the like while providing a moderate cosmetic effect.

Further, when having a suction function, including adding to the rolling with the roller, the cosmetic device is required to be separately equipped with a suction unit such as a vacuum pump, and a cup may also be required for a portion for sucking. This causes a problem of increasing a size of the entire cosmetic device and deteriorating usability, to hinder easy use of the device. Therefore, it has been desired to develop a cosmetic device that is easy to use and has a compact structure while being multi-functional.

The present invention has been made in view of the above problem, and it is an object of the present invention to provide a cosmetic device that serves to dissolve cellulite and the like causing obesity and the like, has a compact structure while being multi-functional, and can be easily used by holding with one hand.

In order to solve the above-mentioned problem, a cosmetic device according to the present invention includes: a main body part provided with an insertion part formed by a space that can be inserted with a user's hand, and a placement part that can be placed with a palm of the user's hand inserted into the insertion part, on an outer surface; a roller disposed at an opening formed on a bottom surface of the main body part and capable of outputting a stimulation signal; and a suction unit contained in the main body part and configured to suck external air from the opening.

In the cosmetic device according to the present invention, in the above-described present invention, a side of the main body part on which the user's hand is inserted is a bill shape in side view in which the insertion part is formed between an upper and lower bill portions, the placement part is an upper surface of the lower bill portion, and the main body part is formed with a finger insertion part that communicates with the insertion part and is formed by an opening hole that can be inserted with a finger of the user.

In the cosmetic device according to the present invention, in the above-described present invention, a lower surface of the upper bill portion and the upper surface of the lower bill portion are formed in a rounded shape convex upward, and in a state where the user inserts a hand into the insertion part and a finger into the finger insertion part, the placement part fits in the palm.

In the above-described present invention, the cosmetic device according to the present invention has an air vent mechanism to discharge sucked air to outside.

In the above-described present invention, the cosmetic device according to the present invention is provided with a drain tank that stores drain contained in the sucked air and is detachable from the main body part.

In the above-described present invention, in the cosmetic device according to the present invention, the roller is attached to a roller cup detachable from the bottom surface of the main body part.

Since the present invention provides a massage function by rolling a roller disposed to the main body part, a suction function with the suction unit, and a stimulation function (an electric stimulation function by applying a stimulation signal (electric signal)) by outputting a stimulation signal with the roller, and all of these functions can be combined and performed in use, the cosmetic device can synergistically exert an effect of dissolving cellulite and the like of user's skin or the like. In addition, in the present invention, so-called fascia release can be easily performed, which efficiently releases fascia adhesion of the user.

Furthermore, while the cosmetic device is multi-functional as described above, the main body part has the compact structure with the suction unit inside and the roller capable of outputting a stimulation signal on the bottom surface that are arranged and integrated, and has the insertion part formed by a space that can be inserted with a user's hand, and the placement part that can be placed with a palm of the user's hand inserted into the insertion part, on the outer surface, allowing the cosmetic device to be easily used by holding with one hand.

DETAILED DESCRIPTION (I) Configuration of a Cosmetic Device 1 According to the Present Invention:

Hereinafter, one aspect of the cosmetic device 1 according to the present invention will be described with reference to the drawings.

Figure 1:
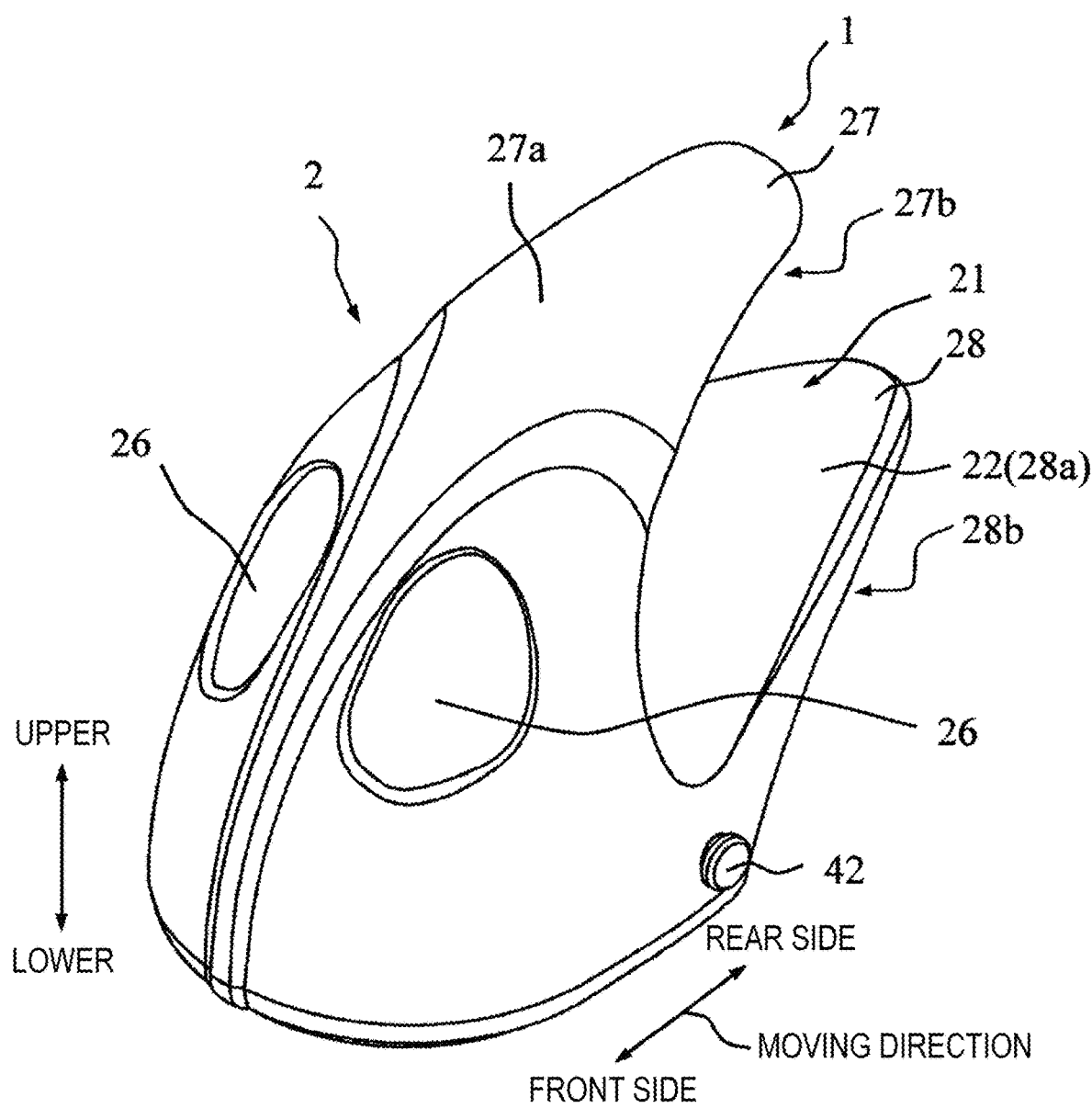
FIG. 1 is a perspective view showing one aspect of a cosmetic device according to the present invention as viewed from above.
Figure 2:
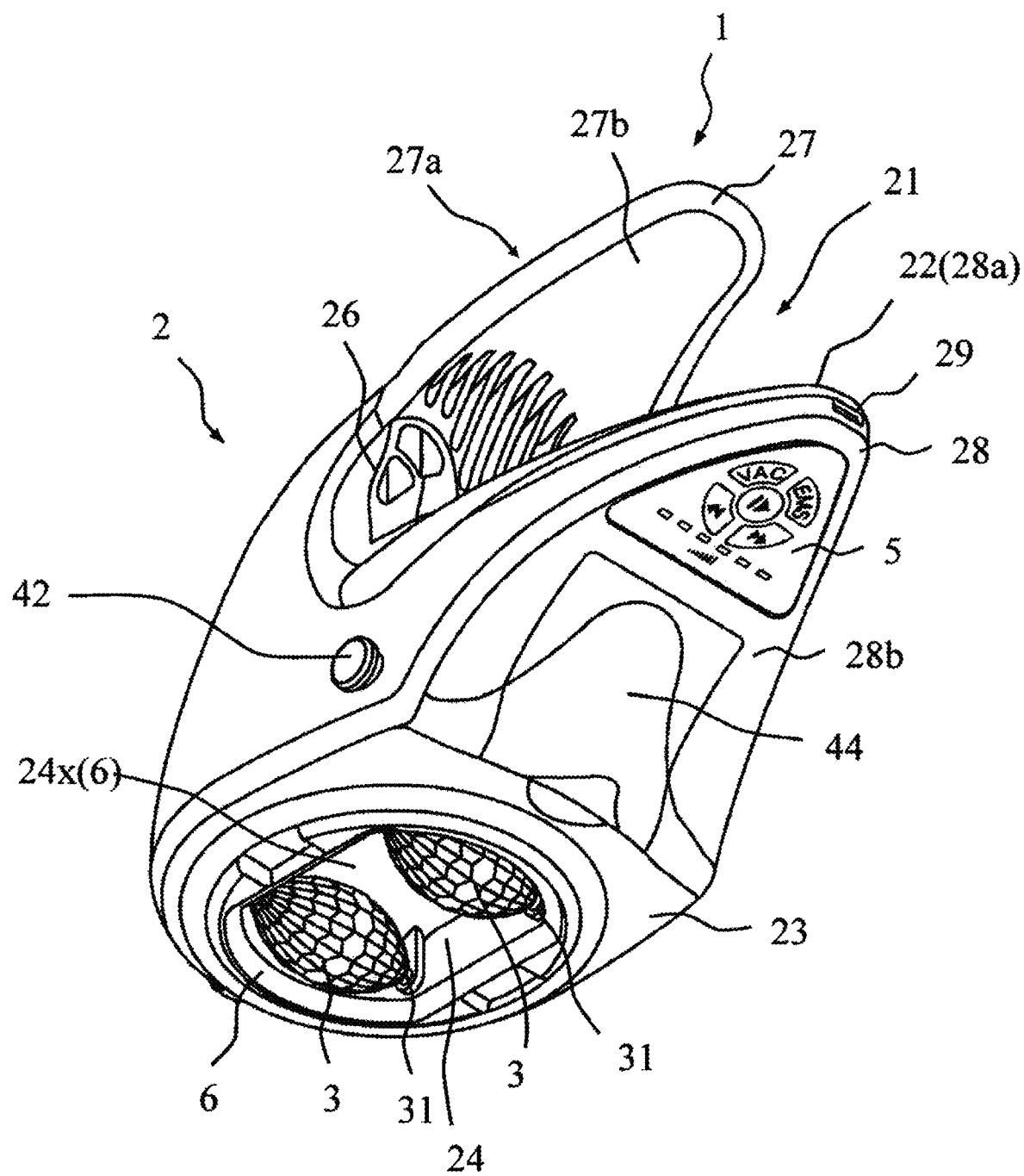
FIG. 2 is a perspective view showing one aspect of the cosmetic device according to the present invention as viewed from below.
Figure 3:
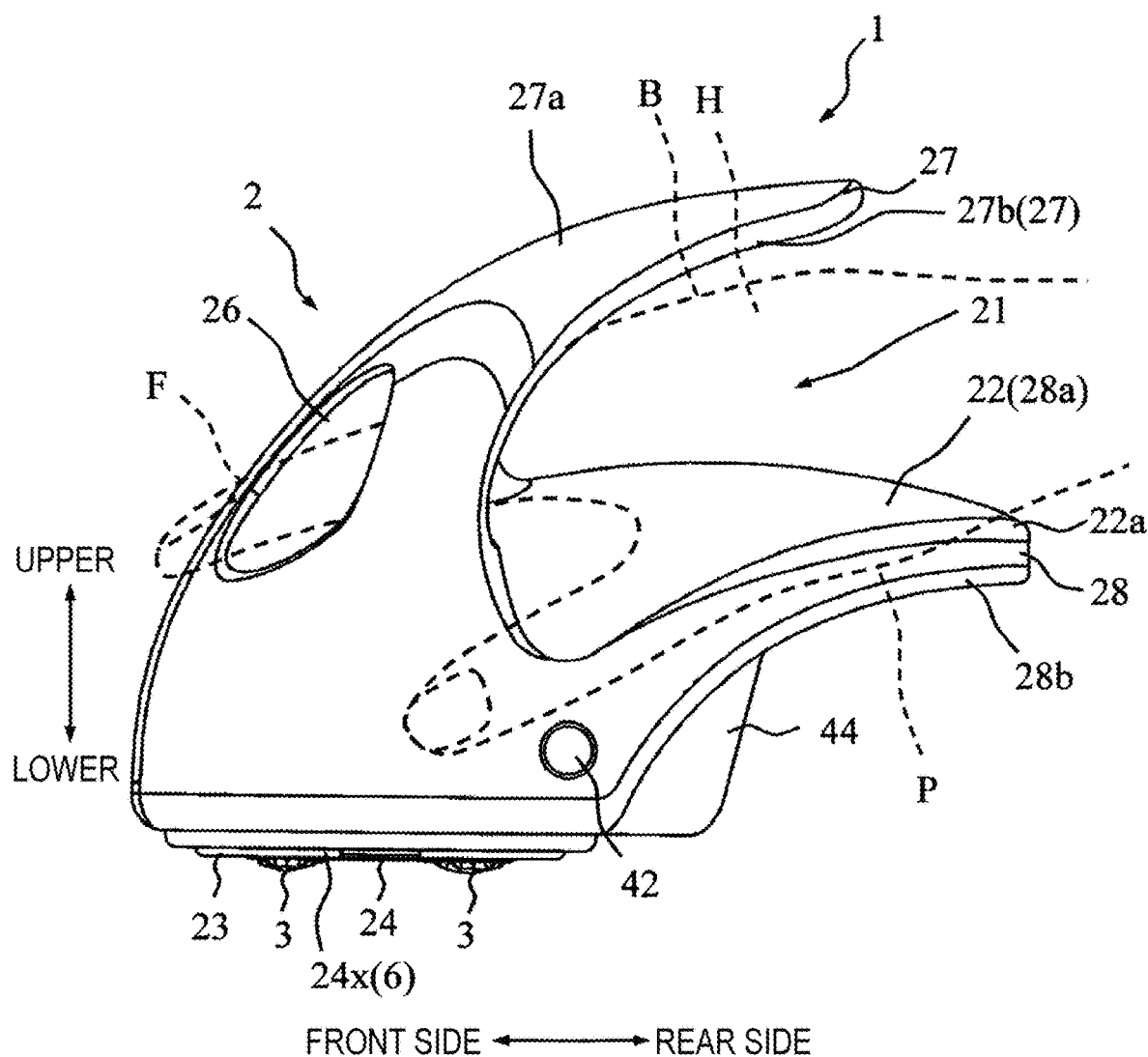
FIG. 3 is a side view of the cosmetic device.
Figure 4:
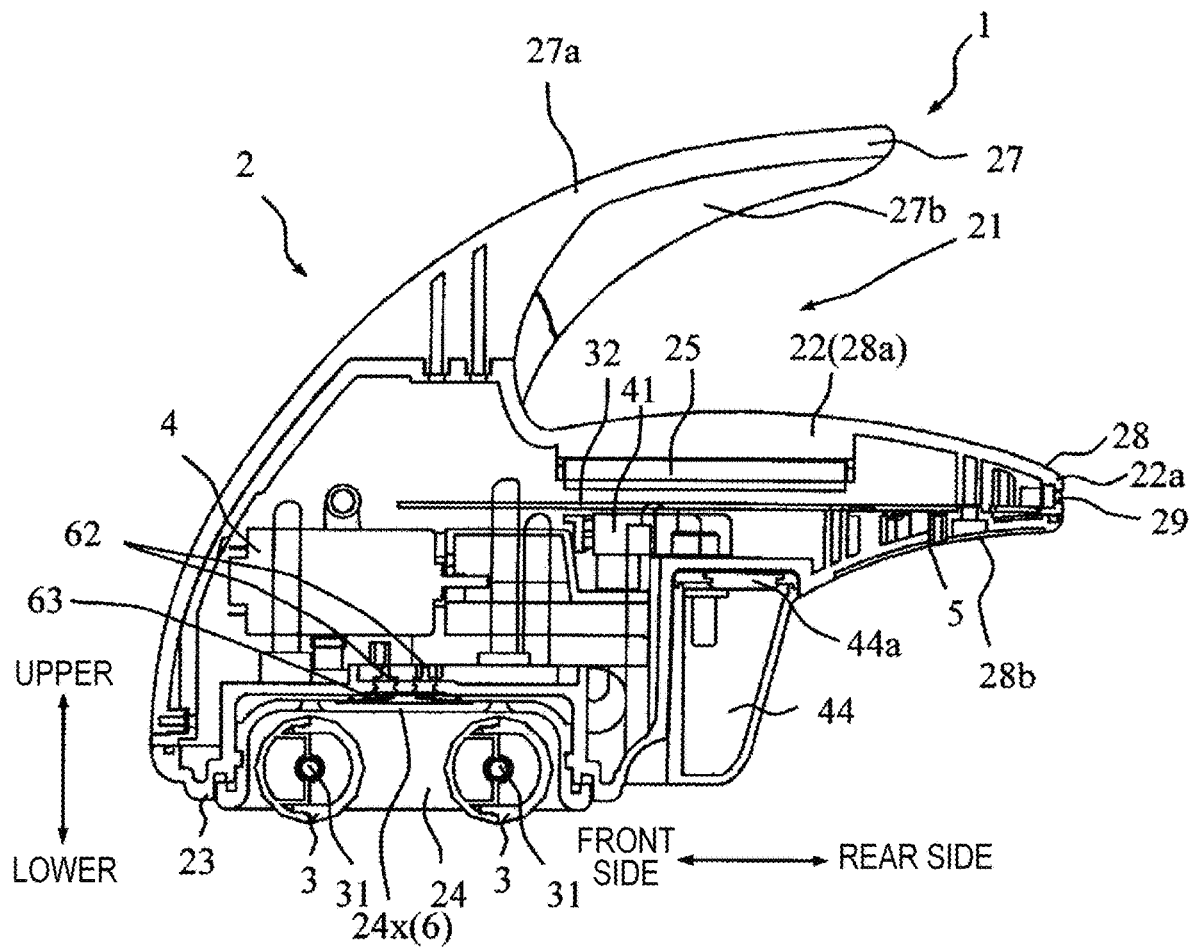
FIG. 4 is a schematic view of an internal structure of the cosmetic device.

FIG. 1 is a perspective view showing one aspect of the cosmetic device 1 according to the present invention as viewed from above, FIG. 2 is a perspective view showing one aspect of the cosmetic device 1 according to the present invention as viewed from below (for upper and lower, see FIGS. 1, 3, and 4, the same applies hereinafter), FIG. 3 is a side view of the cosmetic device 1, and FIG. 4 is a schematic view of an internal structure of the cosmetic device 1. The cosmetic device 1 according to the present invention includes: as a basic configuration, a main body part 2 provided with an insertion part 21 formed by a space that can be inserted with a user's hand H (see FIG. 3), and a placement part 22 that can be placed with a palm of the user's hand (palm) P (see FIG. 3) inserted into the insertion part 21, on an outer surface; a roller 3 disposed at an opening 24 formed on a bottom surface 23 of the main body part 2 and capable of outputting a stimulation signal; and a suction unit (pump) 4 contained in the main body part 2 configured to suck external air from the opening 24. In FIG. 3, the user's hand H holding the cosmetic device 1 is indicated by a dotted line. In addition, FIG. 4 does not illustrate a part of a member incorporated in the main body part 2 of the cosmetic device 1.

The main body part 2 of the cosmetic device 1 is a housing containing a member such as the pump 4 and being arranged with the roller 3 and the like, which may be made from synthetic resin such as ABS resin, for example. The main body part 2 contains the pump 4 serving as a suction unit, and arranged with the roller 3 at the opening 24 formed on the bottom surface 23 as described above. The present embodiment illustrates an aspect in which, as shown in FIGS. 1 to 4, a side of the main body part 2 on which the user's hand H is inserted (a side formed with the insertion part 21, which is on a rear side of the main body part 2 in FIG. 1 or the like (see arrow direction in FIG. 1, the same applies hereinafter)) is formed into a bill shape in side view, and a side opposite to the side inserted with the user's hand H (a front side of the main body part 2 in FIG. 1 or the like (see arrow direction in FIG. 1, the same applies hereinafter)) has a streamline shape connected from the bottom surface 23. The bill shape refers to a state where a bird has opened its bill as shown in FIG. 1 and the like, the opened portion of the bill is the insertion part 21, and there are an upper bill portion 27 above the opened portion and a lower bill portion 28 below as will be described later.

The bill shape of the main body part 2 is formed with the upper bill portion 27 and the lower bill portion 28 with distal ends rounded and sharpened, and formed with the insertion part 21 between the upper bill portion 27 and the lower bill portion 28. The upper bill portion 27 is connected to the streamline shape on the front side of the main body part 2, and both an upper surface 27a and a lower surface 27b are formed in a rounded shape convex upward, in the present embodiment. An upper surface 28a of the lower bill portion is formed in a rounded shape convex upward, and the upper surface 28a can serve as the placement part 22 that can be placed with the palm P of the user when the user's hand H is inserted into the insertion part 21 formed between the upper bill portion 27 and the lower bill portion 28. The cosmetic device 1 according to the present embodiment has a shape that can be used by holding with one hand due to the above-described configuration with the main body part 2 having the pump 4 inside and the roller 3 capable of outputting a stimulation signal on the bottom surface 23 arranged and compactly integrated, while the cosmetic device 1 has various functions.

The present embodiment illustrates a configuration in which there are formed two substantially elliptical finger insertion parts 26, which communicate with the insertion part 21 and are formed by opening holes that can be inserted with a user's finger F, on the front side of the main body part 2. Such a configuration further improves usability with one hand if the placement part 22 fits in the palm P in a state where the user inserts the hand H into the insertion part 21 and the finger F into the finger insertion part 26. When the user's hand H is inserted, the palm P and the back B of the hand to be inserted are easy to fit since the lower surface 27b of the upper bill portion, which is a portion in contact with the palm, and the upper surface 28a of the lower bill portion, which is a portion in contact with a back B of the hand and serves as the placement part 22, are formed into a rounded shape convex upward.

Further, as shown in FIG. 3, forming the upper bill portion 27 shorter than the lower bill portion 28 in the bill shape in side view is desirable since the back B of the hand is even easier to fit as well as the palm P of the user's hand H. As described above, the main body part 2 shown in the present embodiment is formed into a shape with ergonomic design in consideration of usability. It is noted that, while "fit in the palm P" obviously means that an end portion 22a on the insertion side of the placement part 22 (see FIG. 3 and the like) fits in the palm P, "fit in the palm P" also includes a state where the end portion 22a slightly protrudes from the palm P, and a state where the palm P slightly protrudes from the end portion 22a.

When using the cosmetic device 1 constituted by the main body part 2 having such a shape, the user may use the cosmetic device 1, for example, by inserting the hand H into the opened insertion part 21, placing the palm P on the placement part 22 of the lower bill portion 28 (with the finger F inserted into the finger insertion part 26), and holding the cosmetic device 1 with one hand to bring the roller 3 disposed on the bottom surface 23 into contact with the skin, cutis, or the like (skin or the like). Alternatively, the upper bill portion 27 may be held by the hand H to be used.

As shown in FIG. 2, an operation panel 5 is disposed on a lower surface 28b of the lower bill portion. The operation panel 5 disposed on the lower surface 28b of the lower bill portion is for control of turning on/off of power, of a stimulation function with the roller 3 to be described later, and of a suction function and the like for sucking external air with the opening 24 as a suction port.

Figure 5:
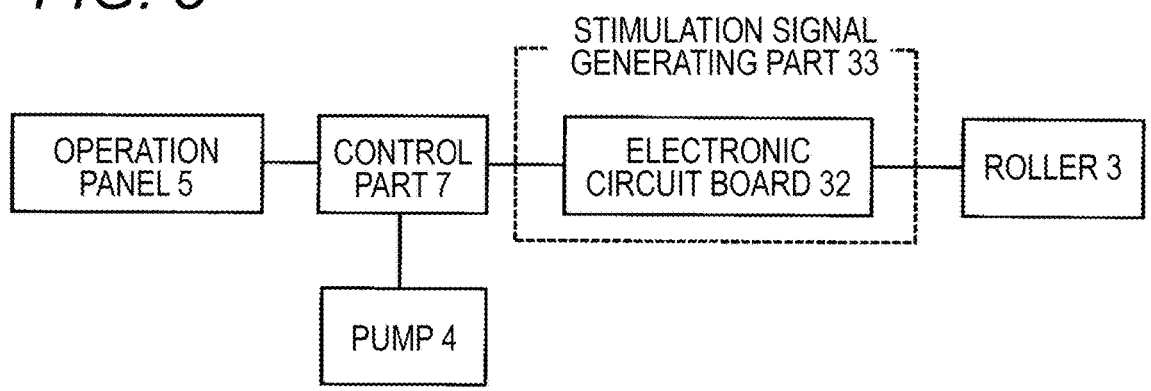
FIG. 5 is an explanatory diagram showing an outline of control with an operation panel.

FIG. 5 is an explanatory diagram showing an outline of control with the operation panel 5. Via a control part 7 incorporated in the main body part 2 of the cosmetic device 1, the operation panel 5 is electrically connected with the pump 4 and the roller 3 connected to a stimulation signal generating part 33 including an electronic circuit board (electric circuit board) 32 (see FIG. 4) provided with an ultrasonic oscillation circuit (not shown), to enable selection of these modes, operation of output level, and the like.

Figure 6:
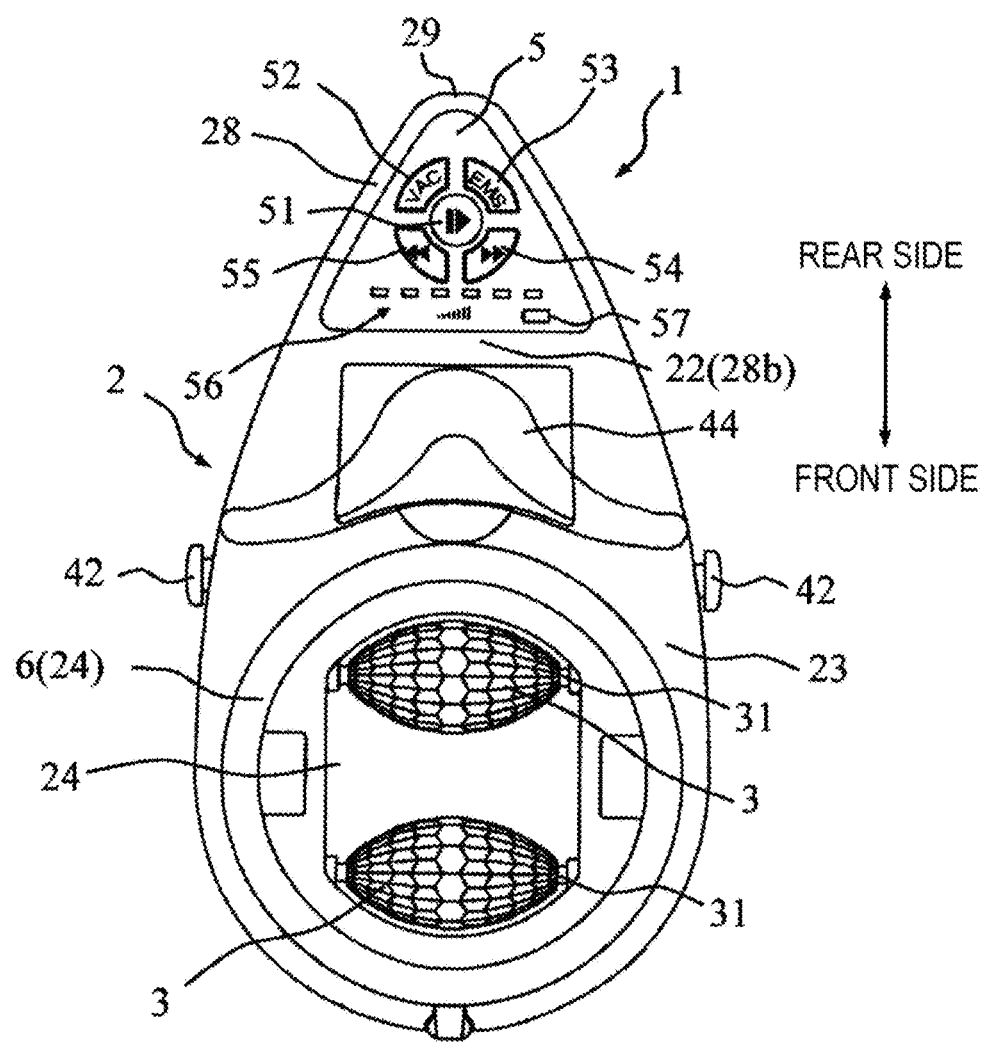
FIG. 6 is a bottom view of the cosmetic device.

FIG. 6 is a bottom view of the cosmetic device 1. As shown in FIG. 6, the operation panel 5 is formed with a power button 51, a suction mode button 52, an EMS mode button 53, a level-up button 54, and a level-down button 55 as the operation buttons, as well as a level indicator lamp 56 and a battery lamp 57 as lamps. It is noted that the operation panel 5 is illustrated as having an EMS mode, which is an example of a mode of a stimulation function (an electrical stimulation function by applying a stimulation signal (electric signal)), and being formed with the EMS mode button 53 as a button to operate the EMS mode, while a mode of the stimulation function is also described as the EMS mode.

The power button 51 is used for operation of turn on/off (ON/OFF) of a power supply of the cosmetic device 1, as well as start, stop, pause, and the like of the suction mode and the EMS mode. For example, pressing the power button 51 for several seconds may turn the power supply "ON", and cause the lamp of the suction mode button 52 and the lamp of the EMS mode button 53 to blink.

For temporarily stopping the operation, for example, pressing the power button 51 during operation may temporarily stop the operation at a level being used in both the suction mode and EMS mode. Further, pressing the power button 51 for several seconds may turn the power supply "OFF".

In addition, while the power source is "ON", pressing the power button 51 again may allow operation in the suction mode to be started. However, the operation state may be changed into the suction mode (where the suction function can be operated) by pressing the suction mode button 52 while the operation state is the EMS mode (where the EMS function can be operated). Conversely, the operation state may be changed into the EMS mode by pressing the EMS mode button 53 while the operation state is the suction mode.

The level-up button 54 is for increasing an output of the mode (suction mode, EMS mode) being operated. For example, the output of the mode is increased by one step each time the button is pressed. The level-down button 55 is for decreasing the output of the mode (suction mode, EMS mode) being operated. For example, the output of the mode is decreased by one step each time the button is pressed.

The level indicator lamp 56 indicates the level of the suction mode and the EMS mode according to the operation state described above, which indicates the levels in six stages in FIG. 6. Further, the battery lamp 57 indicates a remaining amount of a built-in battery (rechargeable battery) 25 (see FIG. 4). For example, the indication may be such that the remaining battery level oo % or more (no problem in use) is indicated by extinguishing the lamp, the remaining battery charge less than oo % (almost time to charge) by lighting the lamp, the remaining battery level less than xx % (necessary to charge immediately) is indicated by blinking the lamp, and the like. It is noted that the above-mentioned oo % and xx % can be optionally determined.

The battery 25 built in the main body part 2 of the cosmetic device 1 can be charged by connecting a device side plug, which is one end of a charging cord (not shown), to an insertion port 29 (see FIG. 2) near the operation panel 5 of the cosmetic device 1, and inserting a power plug, which is another end of the charging cord, into an outlet (not shown).

As shown in FIG. 6 and the like, the opening 24 is formed on the bottom surface 23 of the cosmetic device 1 (main body part 2). In the present embodiment, the opening 24 is formed into a substantially rectangular shape in which a short side is a curved line expanding outward. Further, as shown in FIG. 4, a recess 24x having substantially inverted bowl shape is formed inside the opening 24 (a roller cup 6 described later is attached to the recess 24x as it is), and two rollers 3 are disposed inside the opening 24. In this way, since the portion (recess 24x) disposed with the roller 3 is formed inside the opening 24, a member such as a cup does not appear outside like a conventional cosmetic device.

The roller (rotor) 3 is disposed such that its rotary shaft 31 is orthogonal to a moving direction of the cosmetic device 1 (see the arrow direction in FIG. 1), and the present embodiment shows an aspect in which the roller 3 is formed by a member having a substantially oval shape (substantially entire spindle shape with a central portion having a large diameter) with a surface having a pleated uneven surface. The roller 31 is rotatably attached inside the opening 24 around the rotary shaft 31 that is supported so as to be orthogonal to the moving direction of the cosmetic device 1, and two (a pair of) rollers 3 are supported in parallel.

In the roller 3 rotatably (rollingly) supported on the rotary shaft 31, an outer peripheral portion of the roller 3 is pressed against skin or the like against the body when the user's hand H holds the main body part 2 and presses the bottom surface 23 disposed with the roller 3 against the user's skin or the like. Moving the cosmetic device 1 in the moving direction causes the roller 3 to rotate and roll, which enables massage of the skin or the like, serving to dissolve cellulite and the like. Further, since the skin or the like can be pulled up by rolling the roller 3, cellulite and the like are easily dissolved by the suction function.

In the present embodiment, the roller 3 is attached to the roller cup 6 disposed on the bottom surface 23 of the cosmetic device 1. The roller cup 6 including the roller 3 may be made detachable from the cosmetic device 1 (main body part 2).

Figure 7:
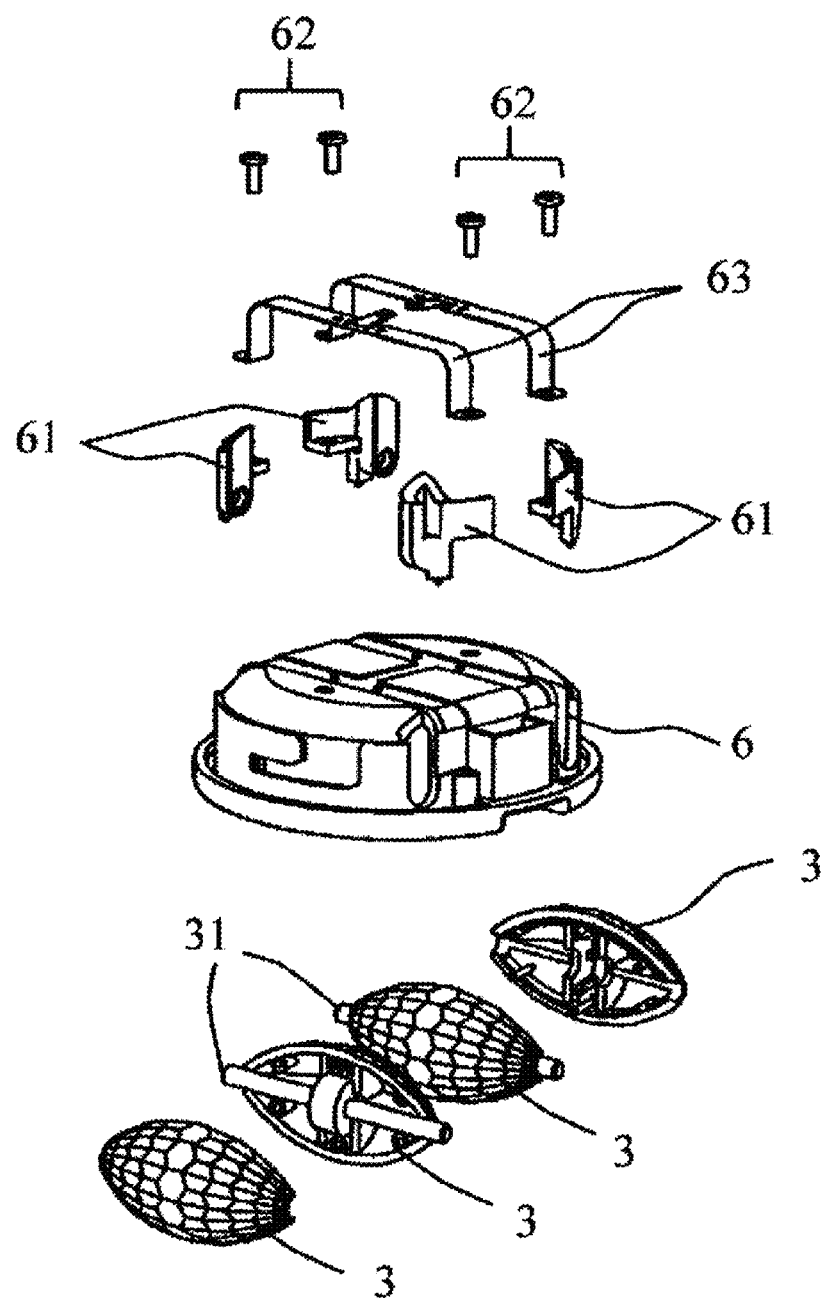
FIG. 7 is an exploded perspective view showing a roller cup.

FIG. 7 is an exploded perspective view showing the roller cup 6. In the present embodiment, the roller cup 6 is provided with a fixing member 61 in addition to the roller 3 having the rotary shaft 31. Further, an electrode member 63 fixedly disposed on the upper surface by a tap 62 is electrically connected to the electronic circuit board 32 (see FIGS. 4 and 5), and is also electrically connected to the roller 3 disposed at the opening 24.

While the roller 3 is used in close contact with the user's skin or the like, it is necessary to clean the roller 3 since gel or the like is often applied to the user's skin or the like as described later, and there may be dirt and the like, or keratin peeled off from the user's skin or the like.

On the other hand, in a state where the roller 3 is attached and fixed to the cosmetic device 1, cleaning is difficult, and water or the like may enter the main body part 2 to cause a failure. Therefore, by enabling the roller cup 6 including the roller 3 to be detachable from the main body part 2 of the cosmetic device 1, it is possible to simply and easily clean the roller 3, and inhibit entering or the like of water into the main body part 2 during cleaning.

In the present invention, the roller 3 disposed at the opening 24 is effective for breaking down and dissolving cellulite and the like by serving as an electrode to generate a stimulation signal, with an electrical stimulation function (may also be simply referred to as a "stimulation function") by applying a stimulation signal (electric signal). As a typical example of the stimulation function, for example, there is known an electrical muscle stimulation (EMS) function effective for dissolving cellulite and the like. Such an EMS function is for stimulating cells and muscles by applying electricity to a human being. In the cosmetic device 1, as the roller 3 comes into contact with the skin or the like, a stimulation signal (low frequency to high frequency stimulation signal) is applied to the skin or the like to stimulate the muscles, enabling the breaking down and dissolving cellulite and the like.

In addition to the massage function by rolling, the cosmetic device 1 uses the roller 3 as a medium to exhibit a stimulation function for generating a stimulation signal, by using the roller 3 as an electrode. Then, since the massage function and the stimulation function can be combined and performed with the suction function using the suction unit 4 (pump 4) that is also effective for dissolving cellulite and the like, the effect of dissolving cellulite and the like can be exerted synergistically.

The stimulation signal is considered such that an electrical stimulation signal of low frequency to high frequency (low frequency pulse, medium frequency pulse, high frequency pulse, and the like) is applied in order to efficiently exhibit the electrical stimulation function by applying the stimulation signal (electric signal). For example, as the electrical stimulation signal, a stimulation signal may be selected and used from frequency ranges of a low frequency (e.g., 1 to 1000 Hz), a medium frequency (e.g., 1000 to 2000 Hz), and a high frequency (e.g., 3000 Hz or higher, such as 3000 to 50000 Hz).

Higher frequency can generally give stimulation to deeper places of the skin or the like, for example, several mm under the skin (cutis) at low frequencies, while several cm at medium frequency. Further, high frequency can give stimulation reaching so-called inner muscles at a depth of 10 cm or more. In view of the above, the range of the frequency of the electrical stimulation signal may be determined in consideration of the depth of the skin or the like to which stimulation is given.

The stimulation signal generating part 33 electrically connected with the roller 3 includes the electronic circuit board 32 provided with the ultrasonic oscillation circuit (not shown), and a stimulation signal from the roller 3 can be applied based on a signal from the ultrasonic oscillation circuit including adjustment of the output level by an operation from the operation panel 5 via the control part 7.

For the waveform of the stimulation signal, it is possible to use various waveforms serving to dissolve cellulite and the like and suitable for cosmetic treatment, and so-called drainage mode or the like may be used. However, there is no particular limitation, and a conventionally known waveform may be used. Moreover, a larger stimulation may be given by using an interference wave formed by combining two or more single waves.

The roller 3 is desirably made of a conductive material so as to generate a stimulation signal and to be capable of applying the stimulation signal to the skin or the like. The conductive materials include, but not limited to, for example, stainless steel (SUS), silver, platinum, aluminum, duralumin, copper, or those plated with chromium plating or the like on these materials.

On the other hand, the suction function with the cosmetic device 1 according to the present invention is performed by using the opening 24 disposed with the roller 3 as a suction port, and activating the pump 4, which is pneumatically communicated with the opening 24 and serves as the suction unit incorporated in the main body part 2, to suck external air. Further, a suction operation of the pump 4, including the output level, is adjusted by the operation from the operation panel 5 via the control part 7.

Figure 8:
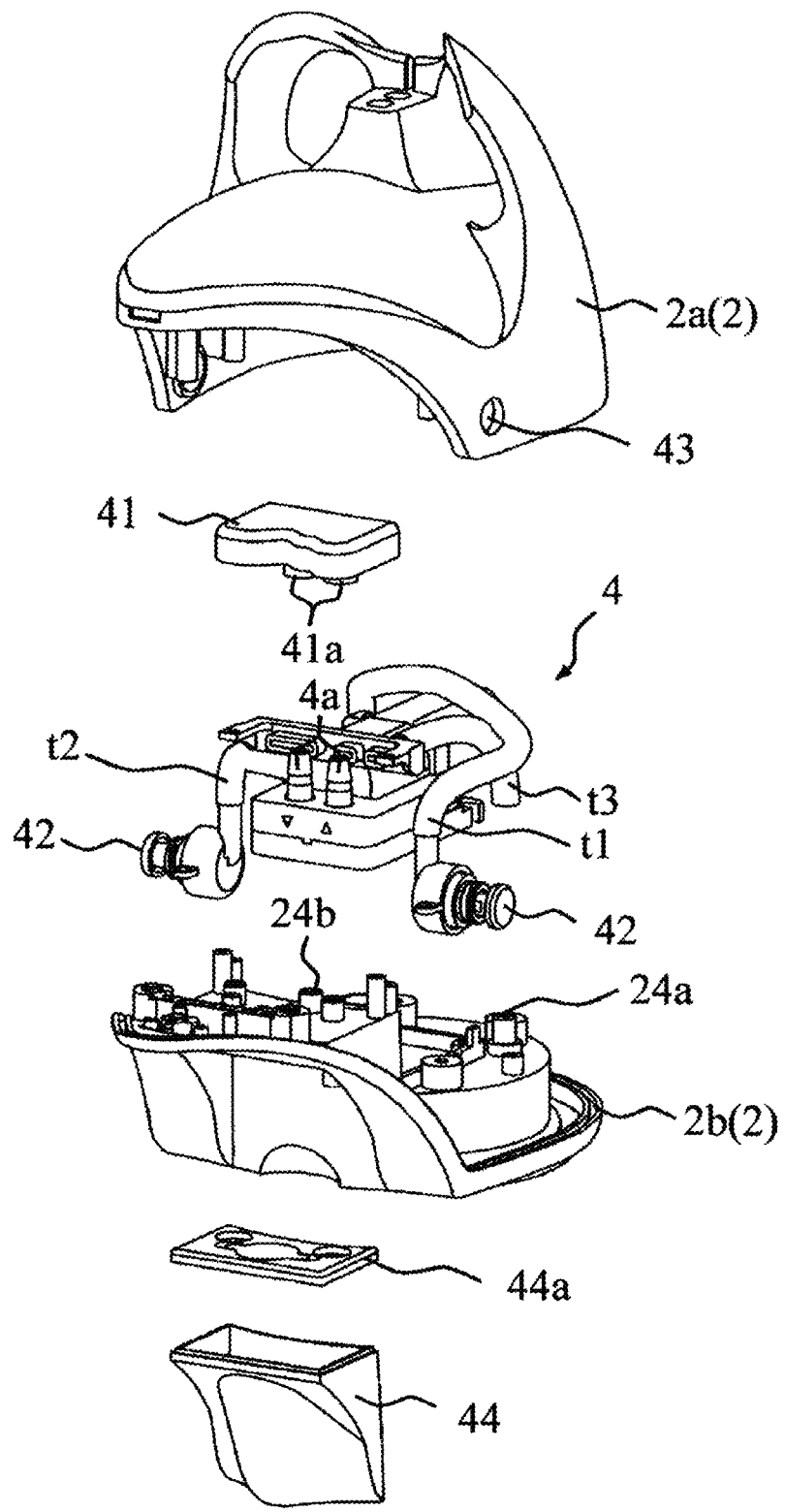
FIG. 8 is a perspective view showing members around a pump.

FIG. 8 is a perspective view showing members around the pump 4. The pump 4 incorporated in the main body part 2 is fixed inside the main body part 2 to be sandwiched between a main body upper part 2a and a main body lower part 2b, with a tank 41 disposed above. Further, a connecting part 4a of the pump 4 is connected and pneumatically communicated with the connecting part 41a of the tank 41. Moreover, a tube t3 is connected and pneumatically communicated with a suction hole 24a. For a capability of the pump 4, a maximum discharge flow rate, a maximum discharge pressure, a maximum vacuum achievement, and the like may be appropriately determined so as to appropriately maintain a vacuum state during suction.

The pump 4 is disposed with an air vent button 42 to be described later, so as to be pneumatically communicated with the pump 4 via tubes t1 and t2. The air vent button 42 is attached so as to appear from a mounting hole 43 formed on the main body upper part 2a to a side surface outside the main body upper part 2a. In the main body part 2, a drain tank 44 is to be detachably attached (the drain tank 44 and a lid body 44a are disassembled in FIG. 8).

A valve (not shown) is attached inside the air vent button 42, and the valve is opened by pressing the air vent button 42. The air vent button 42 is pneumatically communicated with the pump 4 and the like via the tubes t1 and t2, and an air vent mechanism of the cosmetic device 1 is performed by pressing the air vent button 42 to open the internal valve as will be described later, causing air to be drawn from a discharge hole 24b that is pneumatically communicated with the tubes t1 and t2. In this way, when the skin or the like is sucked too much while the suction function is being performed, the sucked air can be discharged to outside by pressing the air vent button 42 in a state where the pump 4 is stopped.

Figure 9:
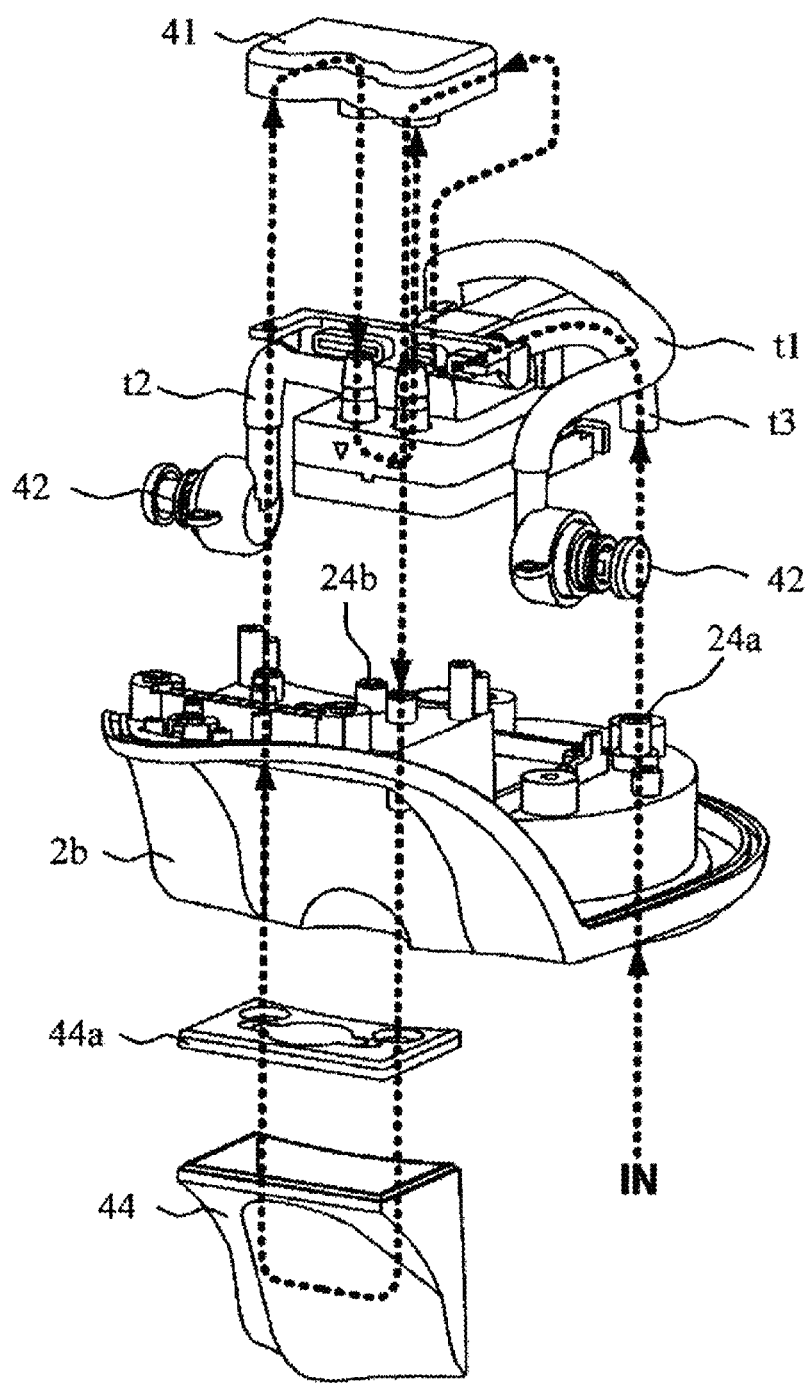
FIG. 9 is an explanatory view showing a path of air sucked from an opening.
Figure 10:
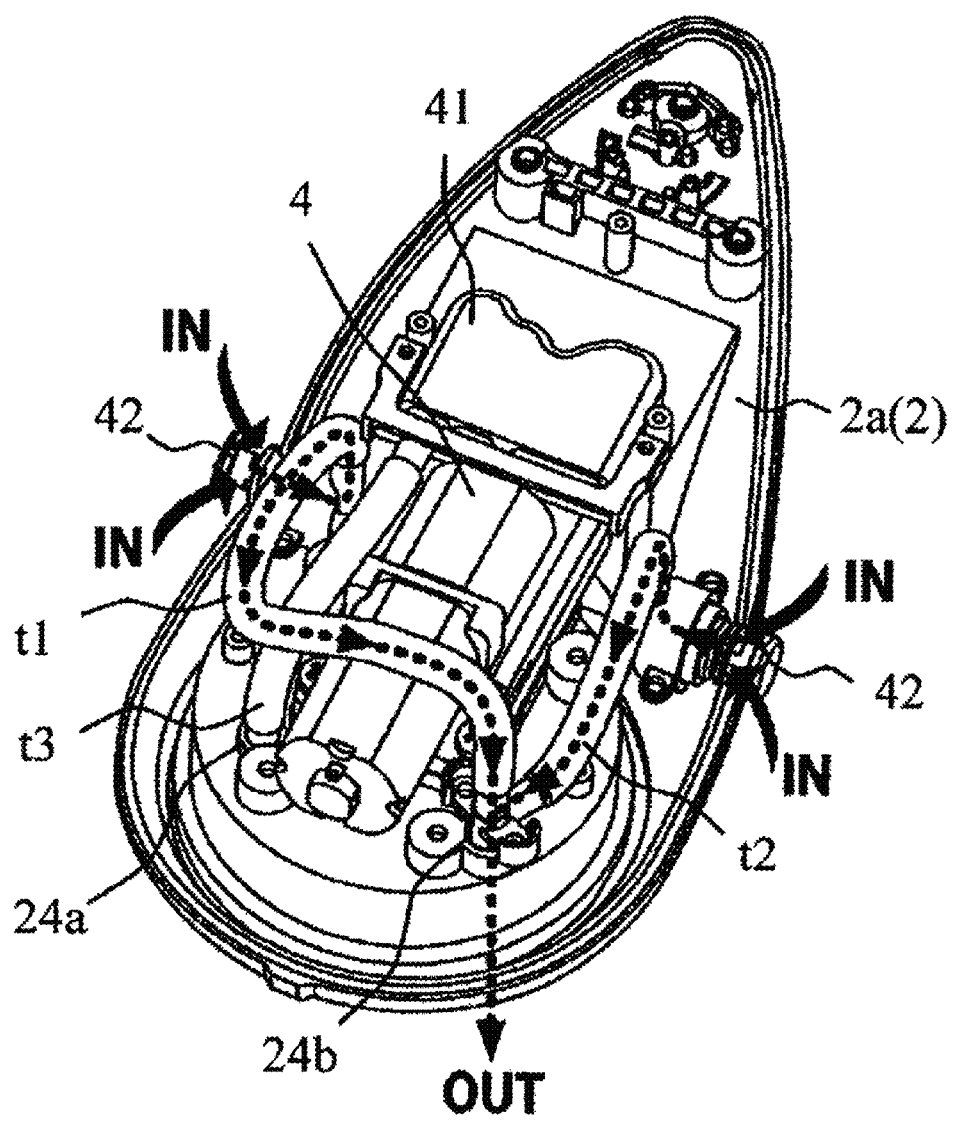
FIG. 10 is an explanatory view showing an air vent mechanism.
Figure 11:
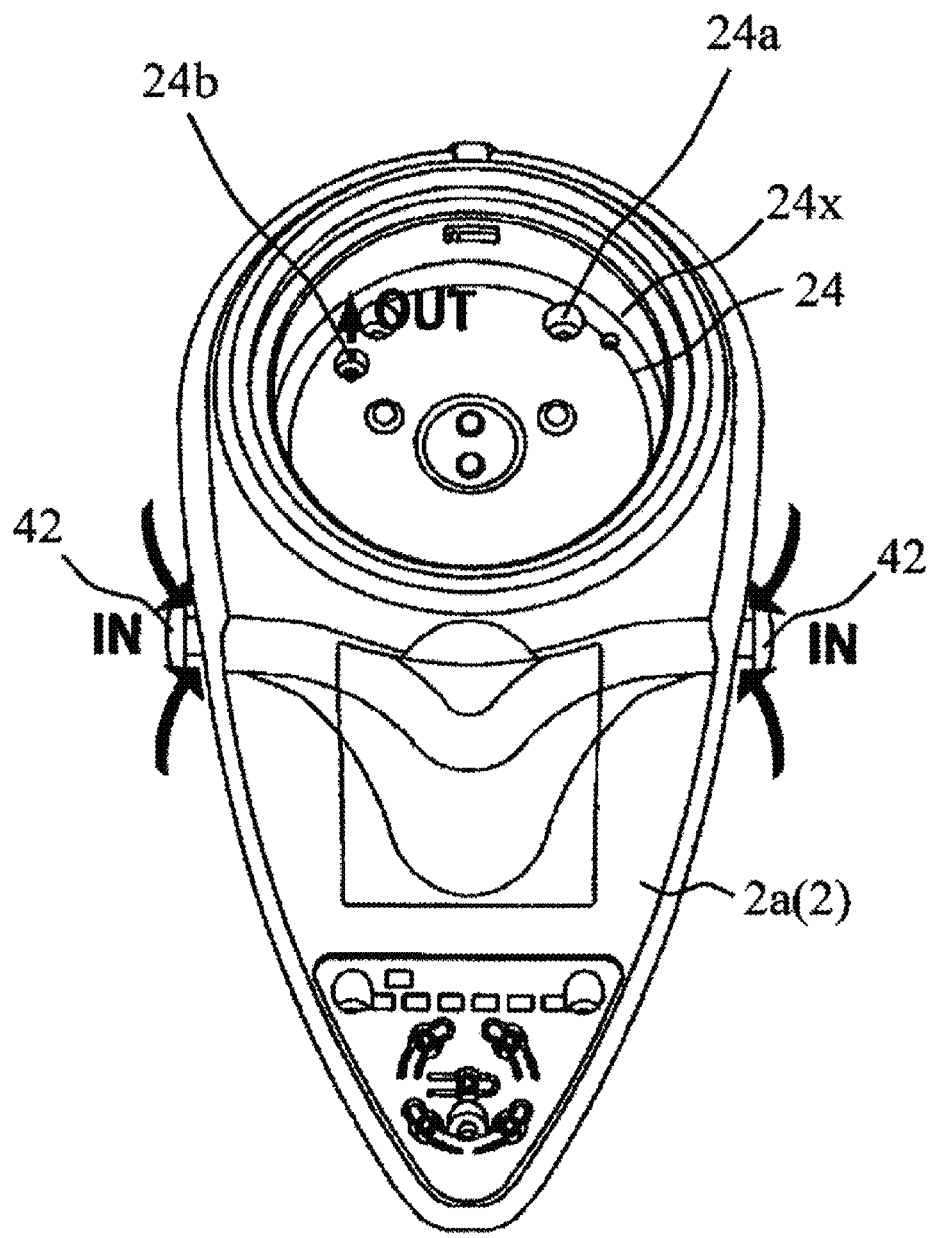
FIG. 11 is an explanatory view showing the air vent mechanism.

FIG. 9 is an explanatory view showing a path of air sucked from the opening 24. In FIG. 9, and FIGS. 10 and 11 to be described later, "IN" indicates suction of air while "OUT" indicates discharge of air. When the pump 4 is operated while the bottom surface 23 of the main body part 2 of the cosmetic device 1 is in close contact with skin or the like, air, gel (not shown) applied to the skin or the like in advance (gel will be described later), dirt of the skin or the like, waste products (gel and the like) are sucked from the suction hole 24a of the opening 24 serving as the suction port formed on the bottom surface 23. The sucked air, gel, and the like (hereinafter may also be simply referred to as "air and the like") move toward the pump 4 located above the suction hole 24a of the opening 24, and pass through the tank 41 via the tube t3 connected to the suction hole 24a, around the pump 4.

The tank 41 changes the path of the sucked air and the like, and the air and the like are introduced into the drain tank 44 that is attached below and pneumatically communicated with the tank 41. The drain tank 44 stores gel or the like, which is an unnecessary portion (drain) among the air and the like to be fed in. The air from which the gel and the like have been removed is discharged upward again from the drain tank 44 and is returned to the tank 41, maintaining the vacuum state.

FIGS. 10 and 11 are explanatory views showing the air vent mechanism. In FIGS. 10 and 11, the operation panel 5 and the roller cup 6 are removed. When the air vent button 42 is pressed with the pump 4 stopped, the valve inside the air vent button 42 is opened (the vacuum state is released), and air is sucked from the air vent button 42 ("IN" indicated by a thick solid line arrow). The air sucked out is discharged from the discharge hole 24b formed at the opening 24 to outside via the tubes t1 and t2 pneumatically communicated with the air vent button 42 ("OUT" indicated by a dotted arrow).

(II) Method for Using the Cosmetic Device 1:

To use the cosmetic device 1, the output level of the suction mode and the EMS mode, which is a mode for the stimulation function, is adjusted by operation of the operation panel 5, then, the bottom surface 23 disposed with the roller 3 is brought into contact with the skin or the like that is to be subjected to the cosmetic treatment, and the cosmetic device 1 is moved along a direction of the arrow in FIG. 1 to rotate and roll the roller 3 inside the opening 24 while being in close contact with the skin or the like.

Due to the suction of the pump 4 and the rolling of the roller 3, the skin or the like with cellulite is slowly pulled up into the opening 24 in the vacuum state. Moreover, the rolling roller 3 takes in the pulled skin or the like, and gives massage to cellulite in a deep part of the skin or the like.

Furthermore, the stimulation function based on the stimulation signal applied by the roller 3 can promote excretion of the waste products. In this manner, massage with the roller 3 and the suction function with the pump 4 give massage to fat cells entangled with collagen fibers to increase fat metabolism, the electric stimulation function by applying the stimulation signal (electric signal) promotes excretion of stuck waste products, making it possible to lead to dissolving cellulite and the like.

Before using the cosmetic device 1, it is desirable to apply gel serving as a lubricant to the user's skin or the like. Applying the gel makes the roller 3 of the cosmetic device 1 more slidable on the skin or the like, enabling suppression of occurrence of redness, internal bleeding, and the like. Further, the gel has an effect of enhancing airtightness between the skin or the like and the roller 3 or the roller cup 6, which complements the suction function with the cosmetic device 1. Furthermore, the gel also serves as a medium for conducting electric stimulation of the stimulation function to the skin or the like sucked in the roller cup 6.

Components composing the gel are not particularly limited, but when water is used as a solvent, for example, there may be used gel containing components such as glycerin, butylene glycol (BG), dipropylene glycol (DPG), carbomer, xanthan gum, arginine, algae extract, Ginkgo biloba extract, grape leaf extract, Pinus sylvestris cone extract, angelica keiskei leaf/stem extract, mate leaf extract, coffee bean extract, PEG-60 almond fatty acid glyceryl, cetyl hydroxyethyl cellulose, methylparaben, allantoin, glycyrrhizic acid 2K, phenoxyethanol, potassium hydroxide, hydrolyzed collagen, water soluble collagen, hypericum erectum extract, arnica flower extract, tilia cordata flower extract, malva sylvestris extract, achillea millefolium extract, salvia officinalis leaf extract, Calendula officinalis flower extract.

(III) Effect of the Present Invention:

According to the present invention described above, in addition to the massage function by rolling the rollers 3 disposed at the opening 24 formed on the bottom surface 23 of the main body part 2, there are provided the suction function with suction unit (pump) 4 effective for dissolving cellulite and the like, and the stimulation function (an electric stimulation function by applying a stimulation signal (electric signal)) by outputting a stimulation signal with the roller 3, and all of these functions can be combined and performed in use. This allows the cosmetic device 1 to synergistically exert the effect of dissolving cellulite and the like of user's skin or the like. In addition, in the present invention, so-called fascia release can be easily performed, which efficiently releases fascia adhesion of the user.

Furthermore, according to the present invention, while the cosmetic device 1 is multi-functional as described above, the main body part 2 has the compact structure with the suction unit (pump) 4 inside and the roller 3 capable of outputting a stimulation signal on the bottom surface 23 that are arranged and integrated, and has the insertion part 21 formed by a space that can be inserted with a user's hand H and the placement part 22 that can be placed with a palm P of the user's hand H inserted into the insertion part 21, on the outer surface. Therefore, the cosmetic device 1 can be easily used by holding with one hand, for example, by inserting the hand H into the insertion part 21 and placing the palm P on the placement part 22.

In the present invention, in use, by giving massage to cellulite at a deep portion of the user's skin with the roller 3 while sucking subcutaneous fat of the user inside the roller cup 6, entangled collagen fibers are separated from the cellulite and gaps are made in the compressed lymphatic vessels and blood vessels, which promotes excretion of waste products, achieving dissolving cellulite and the like including size reduction. In addition, it is possible to enhance a synergistic effect of improving a flow (circulation) of lymph vessels and blood vessels by simultaneously stimulating the sucked cellulite with EMS by the roller 3.

While cellulite affects an appearance of a human body since cellulite causes unevenness on a surface of the skin or the like, dissolving cellulite according to the present invention can eliminates such unevenness. Cellulite generally has a property that it takes a long time to be dissolved while it returns to an original state in a short period of time. However, in the cellulite care according to the present invention as described above, the flow (circulation) of lymph vessels and blood vessels is also improved, enabling dissolving cellulite in a relatively short period of time, and suppressing regeneration of cellulite.

Further, in addition to the cellulite dissolving effect and the like described above, the cosmetic device 1 according to the present invention can efficiently peel (release) fascia adhesion (fascia release). While a place where pain occurs in a human body is called a trigger point, most of trigger points are thought to be a part where fascia has adhered. On the other hand, for so-called myofascial pain syndrome (MPS) caused by a trigger point, there are cases where abnormality is not recognized in an examination, and a place where pain is felt is separated from a place where the pain occurs (trigger point).

Many methods for treating MPS remove pain by fascia release (peeling of adhered fascia) to release adhesion at a trigger point. Fascia release in an aesthetic salon and the like is generally to apply pressure with a massage of a hand technique or the like or movement using a predetermined instrument to conduct treatment such as "pushing" and/or "stretching", which may involve pain.

On the contrary, while having the suction function, the cosmetic device according to the present invention can perform a treatment of stretching fascia with a constant pressure applied by the roller 3 having the EMS function. As a result, physiotherapeutic approach of "peeling while pulling" enables easy fascia release while giving a soft sensation to a user without pain. The cosmetic device 1 according to the present invention is capable of easily releasing adhered fascia that may cause the MPS, in a short time without pain.

In addition to ameliorating the MPS described above, the cosmetic device 1 according to the present invention is also expected to have an effect in improving gliding motility of fascia. Furthermore, various symptoms occurring mainly in muscles and fascia in a whole body can be ameliorated, and as an example of these, an effect of ameliorating distortion and posture of a body, such as bow-legs or knock-knees, can be expected, thereby simultaneously enabling body shaping. As described above, the cosmetic device 1 can provide the above effects by sucking and giving massage with the roller 3 having the EMS function, to peel adhesion of fascia in a relatively short time.

(IV) Modification of Embodiment:

It is to be noted that the above-described aspect shows one aspect of the present invention, and the present invention is not limited to the above-described embodiments. It is needless to say that the present invention includes modifications and improvements within the scope where the configuration of the present invention is included and the object and effect can be achieved. Further, there is no problem even if specific structures, shapes, and the like at the time of practicing the present invention are replaced with other structures, shapes, and the like within the scope where the object and effect of the present invention can be achieved. The present invention is not limited to each of the above-described embodiments, but the present invention includes modifications and improvements within the scope where the object of the present invention can be achieved.

For example, the above-described embodiment illustrates an aspect in which the shape of the roller 3 is the substantially oval shape (entire spindle shape with the central portion having a large diameter) as described above, but there is no problem even if another shape, such as a cylindrical or spherical shape, is adopted as the shape of the roller 3. For the rotation of the roller 3, a driving body may not particularly be provided as described above, or the roller 3 may be rotated electrically (by electric power) by incorporating a driving member (such as a motor) (not shown) in the main body part 2, or the like.

In the above-described embodiment, the shape of the main body part 2 of the cosmetic device 1 has been described with the shape shown in FIG. 1 and the like as an example. However, the main body part 2 can have any shape having the insertion part 21 formed by a space that can be inserted with the user's hand H and the placement part 22 that can be placed with the palm P of the user's hand inserted into the insertion part 21, on the outer surface.

In the above-described embodiment, the description has been made with an example of an aspect in which there are formed the power button 51, the suction mode button 52, the EMS mode button 53, the level-up button 54, and the level-down button 55 as the operation buttons in the operation panel 5, as well as the level indicator lamp 56 and the battery lamp 57 as lamps. However, even for the type of the operation buttons on the operation panel 5 and the like, the operation method of the operation panel 5 formed with the operation buttons and the lamps, or the adjustment method of the suction function and the EMS function as the stimulation function, the present invention is not limited to the details of the above description, but can optionally be determined in consideration of the configuration of the corresponding control part 7 and the level of required functions and the like.

Besides, the specific structure, shape, and the like at the time of practicing the present invention may be other structures or the like within the scope where the object of the present invention can be achieved.

EXAMPLE

Hereinafter, the present invention will be described in more detail based on test examples and the like, but the present invention is not limited thereto.

Test Example 1

Confirmation of cellulite dissolving effect and size reduction effect:

In order to confirm the cellulite dissolving effect and the size reduction effect with the cosmetic device of the present invention, treatment was given to the lower body and the upper body of 10 subjects (female) (Subjects 1 to 10) by using the cosmetic device 1 (cosmetic device of Example 1) having the configuration shown in FIG. 1 and the like, in the following manner. Then, evaluation was made according to the following evaluation items. The treatment in this test (Test Example 1) was performed by the subjects themselves. For Test Example 2, which will be described later, a person other than the subjects performed the treatment on the subjects.

(Evaluation Items)

(1) Measurement of Size:

The size was measured before and after treatment with the cosmetic device, for each part of the subject ("Thickness of upper arms (right, left)", "Around navel", "Above navel", "Below navel", "Buttocks", "Upper thighs (right, left)", "Middle thighs (right, left)", and "Calves (right, left)") (unit is all (cm)). For reference, "Height" and "Weight" of the subjects were also measured.

(2) Measurement of Body Fat Percentage and the Like:

For each item of "Body fat percentage (%)", "Body fat mass (kg)", and "Skeletal muscle mass (kg)", numeric values before and after the treatment were measured by using a body composition analyzer "InBODY 720".

(3) Visual Confirmation with Color Scale:

The effect was visually confirmed by using an ultrasonic dermal measurement device "Derma Lab" (registered trademark) with the color scale (collagen density increases in the order of black→green→blue→red→orange→yellow→white).

(Method for Treatment)

Operation for giving treatment to the lower body and upper body with the cosmetic device was applied by following the description below. Unless otherwise stated, the cosmetic device was used with a surface provided with the roller facing the subject, and the roller was rotated by moving the cosmetic device. Further, the cosmetic device was used with gel appropriately applied to a portion to be subjected to the treatment, of the subject. The treatment was basically given for each item for about 5 to 10 minutes for one time, and this was performed 4 times a week×5 weeks (a total of 20 times). Suction of air and generation of stimulation signal by the roller were performed during the treatment to cause the suction function and the EMS function to be exhibited, and output modes of these were appropriately adjusted in accordance with a suitable output mode (output level) corresponding to details of the treatment.

(Treatment: Lower Body)

(A) Soles:

Suction was performed with the cosmetic device placed at a center of the sole of the subject's foot, and when the subject felt the suction, the cosmetic device was slowly moved back and forth toward the heel, on the sole of the foot. Further, the same operation was performed on the arch line.

(B) Front Side of Under Knees:

The cosmetic device was moved from the ankle to the knee, against an outer side of under the subject's knee.

(C) Calves:

The cosmetic device was moved from the ankle to the knee, against an inner side of under the subject's knee.

(D) Around Knees:

The cosmetic device was moved so as to make a flow upward, against around the subject's knee (side, upper).

(E) Front Thighs:

The cosmetic device was moved so as to make a flow toward the inguinal lymph node, against the outer thigh of the subject's.

(F) Inner Thighs:

The cosmetic device was moved so as to make a flow toward the inguinal lymph node, against the inner thigh of the subject.

(G) Back Thighs:

The cosmetic device was moved so as to make a flow toward the buttocks, against the back thigh of the subject's.

(H) Buttocks:

The cosmetic device was moved upward, against subject's buttocks so as to lift the buttocks.

(Treatment: Upper Body)

(A) Abdomen (1):

The cosmetic device was moved toward the inguinal lymph node from the waist, along the subject's ilium (while being aware of a prominence of the pelvis). Further, the cosmetic device was moved from outside toward a center along the ribs.

(B) Abdomen (2):

The cosmetic device was moved from outside toward a center so as to form a "waist".

(C) Abdomen (3):

The cosmetic device was moved toward the inguinal lymph node of the subjects so as to make a flow on the entire abdomen.

(D) Around Lower Back:

The cosmetic device was moved from the lower back to the buttocks of the subject so as to relax the lower back.

(E) Inner Arm

The cosmetic device was uniformly moved against the entire inner side of the lower arm, from the wrist toward an inner side of the elbow. Further, the cosmetic device was uniformly moved from the inner side of the elbow toward the armpit, against entire inner side of under the upper arm.

(F) Outer Arm

The cosmetic device was uniformly moved against the lower arm, from the wrist toward the elbow. Further, the cosmetic device was moved from the elbow to the armpit, against an outer side of the upper arm.

(Measurement Result)

TABLE 1

| | | Measurement (cm) | | | | | | | | | | | |
|---|---|---|---|---|---|---|---|---|---|---|---|---|---|
| | | Thickness of upper arms | | Around navel | Above navel | Below navel | Buttocks | Upper thighs | | Middle thighs | | Calves | |
| Subject | | Right | Left | | | | | Right | Left | Right | Left | Right | Left |
| 1 | Before treatment | 30.5 | 29.7 | 83.2 | 73.9 | 87.7 | 98.1 | 56.8 | 57.8 | 45.8 | 47.2 | 36.5 | 37.3 |
| | After treatment | 29.4 | 28.8 | 81.2 | 72.2 | 83.9 | 96.0 | 55.8 | 55.9 | 42.6 | 43.8 | 35.6 | 36.4 |
| | Difference | −1.1 | −0.9 | −2.0 | −1.7 | −3.8 | −2.1 | −1.0 | −1.9 | −3.2 | −3.4 | −0.9 | −0.9 |
| 2 | Before treatment | 28.8 | 27.9 | 80.8 | 70.6 | 84.1 | 99.0 | 60.8 | 60.3 | 54.4 | 55.0 | 38.1 | 37.7 |
| | After treatment | 27.8 | 27.3 | 75.3 | 67.8 | 79.8 | 97.8 | 57.9 | 58.3 | 51.2 | 51.3 | 36.2 | 36.0 |
| | Difference | −1.0 | −0.6 | −5.5 | −2.8 | −4.3 | −1.2 | −2.9 | −2.0 | −3.2 | −3.7 | −1.9 | −1.7 |
| 3 | Before treatment | 37.4 | 37.1 | 102.6 | 95.1 | 106.7 | 108.7 | 62.1 | 62.4 | 57.3 | 56.5 | 38.9 | 38.0 |
| | After treatment | 36.8 | 36.7 | 101.8 | 95.1 | 103.6 | 106.1 | 60.4 | 61.2 | 55.8 | 55.7 | 38.8 | 37.9 |
| | Difference | −0.6 | −0.4 | −0.8 | — | −3.1 | −2.6 | −1.7 | −1.2 | −1.5 | −0.8 | −0.1 | −0.1 |
| 4 | Before treatment | 26.8 | 27.1 | 75.5 | 70.5 | 81.3 | 91.0 | 53.1 | 53.9 | 52.6 | 52.8 | 36.5 | 36.4 |
| | After treatment | 25.9 | 25.5 | 72.6 | 68.8 | 79.2 | 87.8 | 51.5 | 51.9 | 50.5 | 50.9 | 35.9 | 35.3 |
| | Difference | −0.9 | −1.6 | −2.9 | −1.7 | −2.1 | −3.2 | −1.6 | −2.0 | −2.1 | −1.9 | −0.6 | −1.1 |
| 5 | Before treatment | 28.8 | 28.7 | 80.5 | 69.5 | 87.5 | 93.6 | 53.6 | 54.1 | 47.4 | 46.8 | 33.1 | 33.0 |
| | After treatment | 28.1 | 28.0 | 77.2 | 67.3 | 84.3 | 92.4 | 52.4 | 52.9 | 45.3 | 45.8 | 32.0 | 31.9 |
| | Difference | −0.7 | −0.7 | −3.3 | −2.2 | −3.2 | −1.2 | −1.2 | −1.2 | −2.1 | −1.0 | −1.1 | −1.1 |
| 6 | Before treatment | 23.3 | 24.5 | 78.4 | 67.8 | 80.4 | 90.5 | 49.0 | 49.5 | 40.9 | 41.2 | 32.6 | 32.8 |
| | After treatment | 23.0 | 23.9 | 72.5 | 65.8 | 80.9 | 89.6 | 46.9 | 47.9 | 38.3 | 39.7 | 31.8 | 32.4 |
| | Difference | −0.3 | −0.6 | −5.9 | −2.0 | 0.5 | −0.9 | −2.1 | −1.6 | −2.6 | −1.5 | −0.8 | −0.4 |

TABLE 1-continued

| | | | | | | | | | | | | | |
|---|---|---|---|---|---|---|---|---|---|---|---|---|---|
| 7 | Before treatment | 27.6 | 26.8 | 77.6 | 80.5 | 87.8 | 95.9 | 53.2 | 53.8 | 46.4 | 46.3 | 38.1 | 37.4 |
| | After treatment | 27.0 | 26.8 | 76.8 | 76.2 | 83.3 | 95.4 | 51.8 | 52.5 | 43.6 | 45.6 | 37.5 | 37.0 |
| | Difference | −0.6 | 0.0 | −0.8 | −4.3 | −4.5 | −0.5 | −1.4 | −1.3 | −2.8 | −0.7 | −0.6 | −0.4 |
| 8 | Before treatment | 26.0 | 25.8 | 70.5 | 77.3 | 83.7 | 89.1 | 50.5 | 50.2 | 41.8 | 42.4 | 32.8 | 32.7 |
| | After treatment | 24.5 | 25.5 | 70.0 | 71.6 | 85.0 | 89.4 | 48.1 | 49.8 | 41.6 | 41.9 | 33.0 | 32.8 |
| | Difference | −1.5 | −0.3 | −0.5 | −5.7 | 1.3 | 0.3 | −2.4 | −0.4 | −0.2 | −0.5 | 0.2 | 0.1 |
| 9 | Before treatment | 31.2 | 30.8 | 87.7 | 76.4 | 93.6 | 96.4 | 60.0 | 59.0 | 53.5 | 52.5 | 36.3 | 36.5 |
| | After treatment | 30.3 | 30.2 | 83.0 | 74.4 | 87.1 | 96.3 | 59.6 | 59.2 | 51.4 | 52.0 | 36.3 | 36.5 |
| | Difference | −0.9 | −0.6 | −4.7 | −2.0 | −6.5 | −0.1 | −0.4 | 0.2 | −2.1 | −0.5 | 0.0 | 0.0 |
| 10 | Before treatment | 28.1 | 27.9 | 87.9 | 78.1 | 89.5 | 94.9 | 56.4 | 56.1 | 50.1 | 50.0 | 35.3 | 34.8 |
| | After treatment | 27.8 | 27.8 | 85.9 | 77.6 | 86.0 | 93.3 | 55.4 | 55.8 | 49.4 | 49.3 | 34.7 | 34.8 |
| | Difference | −0.3 | −0.1 | −2.0 | −0.5 | −3.5 | −1.6 | −1.0 | −0.3 | −0.7 | −0.7 | −0.6 | 0.0 |

| Subject | | Measurement with InBODY | | | | |
|---|---|---|---|---|---|---|
| | | Body fat percentage (%) | Body fat mass (kg) | Skeletal muscle mass (kg) | Weight (kg) | Height (cm) |
| 1 | Before treatment | 31.0 | 19.6 | 23.5 | 63.4 | 163.0 |
| | After treatment | 30.3 | 19.1 | 23.5 | 62.9 | — |
| | Difference | −0.7 | −0.5 | — | −0.5 | — |
| 2 | Before treatment | 35.2 | 21.8 | 21.4 | 61.9 | 164.0 |
| | After treatment | 33.9 | 20.4 | 21.3 | 60.1 | — |
| | Difference | −1.3 | −1.4 | −0.1 | −1.8 | — |
| 3 | Before treatment | 38.9 | 32.1 | 27.9 | 82.4 | 166.0 |
| | After treatment | 38.4 | 31.7 | 28.1 | 82.4 | — |
| | Difference | −0.5 | −0.4 | 0.2 | — | — |
| 4 | Before treatment | 36.8 | 20.6 | 18.8 | 56.0 | 154.0 |
| | After treatment | 35.5 | 19.3 | 18.9 | 54.5 | — |
| | Difference | −1.3 | −1.3 | 0.1 | −1.5 | — |
| 5 | Before treatment | 30.8 | 17.4 | 21.3 | 56.4 | 159.0 |
| | After treatment | 30.7 | 17.2 | 21.1 | 55.9 | — |
| | Difference | −0.1 | −0.2 | −0.2 | −0.5 | — |
| 6 | Before treatment | 27.1 | 13.4 | 19.4 | 49.6 | 159.0 |
| | After treatment | 25.5 | 12.7 | 19.9 | 49.9 | — |
| | Difference | −1.6 | −0.7 | 0.5 | 0.3 | — |
| 7 | Before treatment | 28.9 | 18.0 | 24.4 | 62.4 | 160.0 |
| | After treatment | 27.6 | 17.0 | 24.6 | 61.7 | — |
| | Difference | −1.3 | −1.0 | 0.2 | −0.7 | — |
| 8 | Before treatment | 26.4 | 14.2 | 21.6 | 53.9 | 163.0 |
| | After treatment | 24.4 | 13.1 | 22.2 | 53.6 | — |
| | Difference | −2.0 | −1.1 | 0.6 | −0.3 | — |
| 9 | Before treatment | 36.6 | 21.9 | 20.5 | 59.8 | 152.0 |
| | After treatment | 38.6 | 23.3 | 19.9 | 60.2 | — |
| | Difference | 2.0 | 1.4 | −0.6 | 0.4 | — |
| 10 | Before treatment | 34.0 | 20.3 | 21.2 | 59.6 | 157.0 |
| | After treatment | 34.3 | 20.3 | 21.1 | 59.3 | — |
| | Difference | 0.3 | 0.0 | −0.1 | −0.3 | — |

The above-mentioned treatment was performed, and the measurement results of (1) and (2) before and after the treatment are shown in Table 1. As shown in Table 1, as a result of performing the above treatment using the cosmetic device, most of numeric values of the measured results for each part listed in (1) were decreased. In addition, numeric values of most of the items listed in (2) were also decreased. In Table 1, skeletal muscle mass was slightly increased or slightly decreased. Achievement of size reduction without excessive decrease in skeletal muscle mass may be considered to prove an absence of dietary restriction, showing that the size reduction was achieved without dietary restriction.

In addition to the fact that cellulite was dissolved as described later, it was confirmed that size reduction was achieved by dissolving cellulite. It was particularly confirmed that the body fat percentage remarkably decreased in most of the subjects, and it is considered that the cellulite dissolving effect with the treatment using the cosmetic device is largely related to the reduction of body fat mass.

Figure 12:
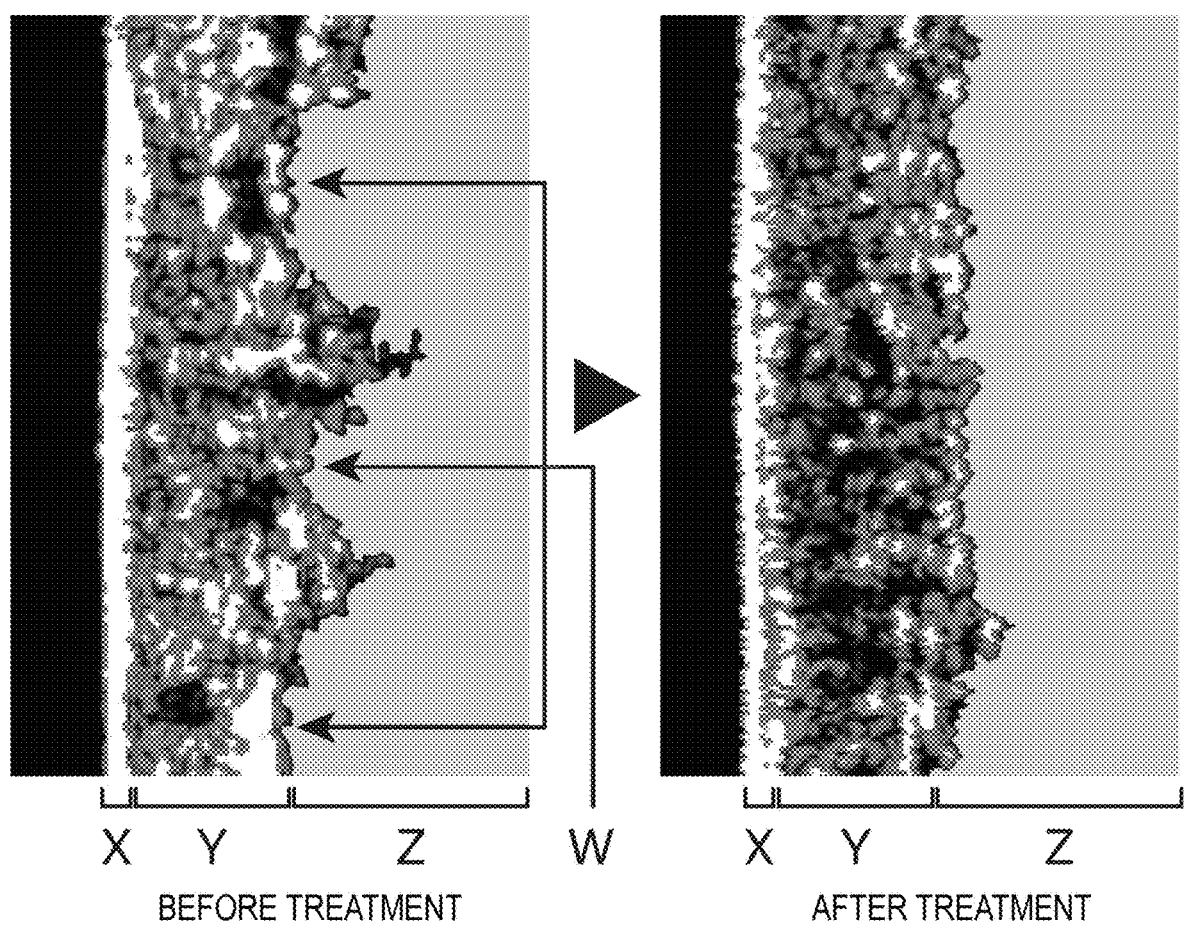
FIG. 12 is a view showing a measurement result with an ultrasonic dermal measurement device in Test Example 1.

Measurement result (measurement site: back thigh) with the ultrasonic dermal measurement device "Derma Lab" is shown in FIG. 12. In the measurement, a small amount of commercially available baby oil was applied to the measurement site, and a probe was placed on the skin to momentarily irradiate ultrasonic waves. This is to utilize a characteristic of reflecting (echoing) on a surface having a different property against ultrasonic waves, by applying ultrasonic waves from the probe to the skin surface. The reflection does not occur in fat and muscles, and a boundary surface between a dermis layer and subcutaneous fat can be visually displayed. In FIG. 12, W represents cellulite entangled with collagen fibers, X represents epidermis, Y represents a dermis layer, and Z represents subcutaneous fat.

As shown in FIG. 12, it was confirmed that the unevenness disappeared, the boundary surface between the dermis layer and the subcutaneous fat became flat, and reduction or dissolving of cellulite, from the measurement result. It is considered that, before the treatment with the cosmetic device, while fat cells entangled with collagen fibers compressed the dermis layer, and boundary surface became uneven and was no longer flat, the treatment with the cosmetic device released the compressed state and improved the boundary surface between the dermis layer and subcutaneous fat to be flat. Although FIG. 12 is an example, such reduction was confirmed in most of the subjects.

In FIG. 12, a phenomenon that a white portion seems to be slightly reduced is resulted from that hardened collagen fibers entangled to cellulite were peeled off by a massaging action using the cosmetic device, and excretion was promoted by the EMS stimulation. Therefore, it is considered that connections of the collagen fibers are properly aligned with each other, and density of collagen is made uniform.

Test Example 2

Confirmation of Ameliorating Effect of Bow-Legs and Knock-Knees by Fascia Release (Confirmation of Fascia Release Effect):

In order to confirm the effect of ameliorating bow-legs and knock-knees by fascia release, a state of the subject (female) was checked before and after being subjected to the following treatment by using the cosmetic device 1 (cosmetic device of Example 1) having the configuration shown in FIG. 1 and the like described above. The treatment was given for one time (15 minutes), and as with the Test Example 1, the cosmetic device was used with the surface provided with the roller facing the subject, and the roller was rotated by moving the cosmetic device, unless otherwise stated. Further, the cosmetic device was used with gel appropriately applied to a portion to be subjected to the treatment, of the subject. Suction of air and generation of stimulation signal by the roller were performed during the treatment to cause the suction function and the EMS function to be exhibited, and output modes of these were appropriately adjusted in accordance with a suitable output mode (output level) corresponding to details of the treatment.

(1) Treatment: Back Line (Foot (Sole)):

First, as a pretreatment, the following hand technique was performed. While the subject is lying on the stomach with a rolled bath towel or the like placed under the ankle of the subject, overlapped thumbs of the person giving the treatment were slowly moved from a center to just before the metatarsal bone, while firmly applying pressure.

Next, while the cosmetic device is sucking just before the metatarsal bone and being stopped, movement of "bending and returning" toward the shin was repeatedly given to the toes of the subject (repeated about 5 times).

While the cosmetic device was moved little by little toward the heel, the movement of "bending and returning" toward the shin was repeated. Again, this was repeated about five times.

From the heel toward the metatarsal bone, the cosmetic device was slowly moved as if sweeping. The cosmetic device was slowly moved from outside toward inside on the lateral arch of the metatarsal and the lateral arch on the heel. Finally, the entire sole was stroked with a palm.

(2) Treatment: Back Line (Leg (Back Side)):

First, as a pretreatment, the following hand technique was performed. That is, gel (treatment gel) was spread with both hands over the entire leg. After the gel was spread, both thumbs were moved upward on the Achilles tendon to make a flow in one direction. Next, four fingers were moved so as to lift both sides of the malleolus to make a flow. In addition, with a first made with one hand, the entire calf was massaged.

With the leg of the subject slightly bent in a V-shape, the cosmetic device was slowly moved so as to connect a line above the outer malleolus toward the knee so as to make a flow for three times. Moreover, the line was divided into four, and the cosmetic device was stopped while sucking. At the same time, bending and stretching of the ankle was repeated on the subjects about five times. Finally, the cosmetic device was slowly moved along the same line to make a flow again, and this was repeated for three times.

The cosmetic device was placed vertically against the (outer) gastrocnemius, and slightly moved from outside toward the center. Next, the cosmetic device was slowly moved against the back thigh, so as to relax above the lymph node. Further, the cosmetic device was slowly moved upward (direction toward the buttocks) from a boundary of the hamstrings (middle of the back thigh).

The cosmetic device was slowly moved from the outer thigh (iliotibial band) toward the waist (ilium). Next, the cosmetic device was stopped while sucking the inner thigh (semimembraneous muscle). At the same time, the subject slowly bent and stretched the knee. The above-described treatment with the cosmetic device stopped and sucking was repeatedly performed while the cosmetic device was gradually moved upward (direction toward the buttocks). Finally, the entire foot was rubbed with a palm. The above treatment was similarly given to the opposite leg.

Figure 13:
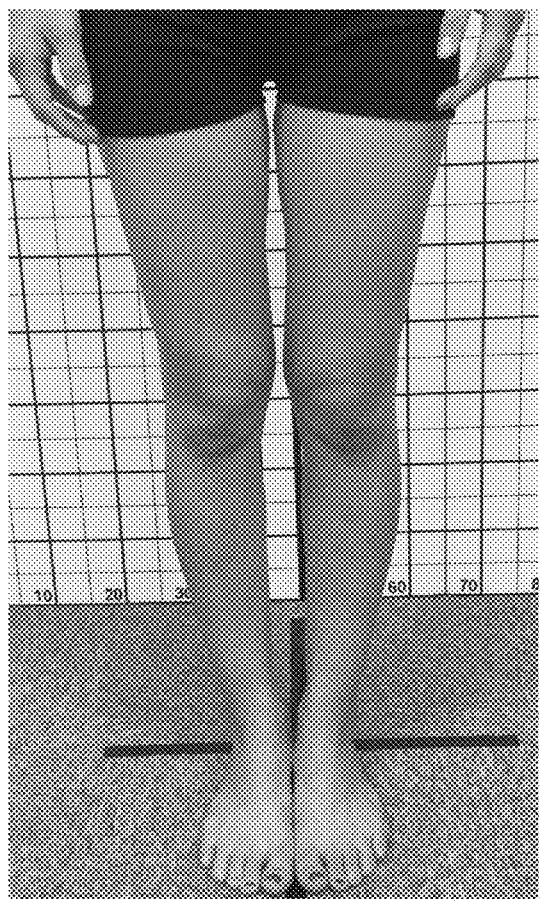
FIG. 13 is a view showing a measurement result of external appearance of legs of a subject in Test Example 2.
Figure 13:
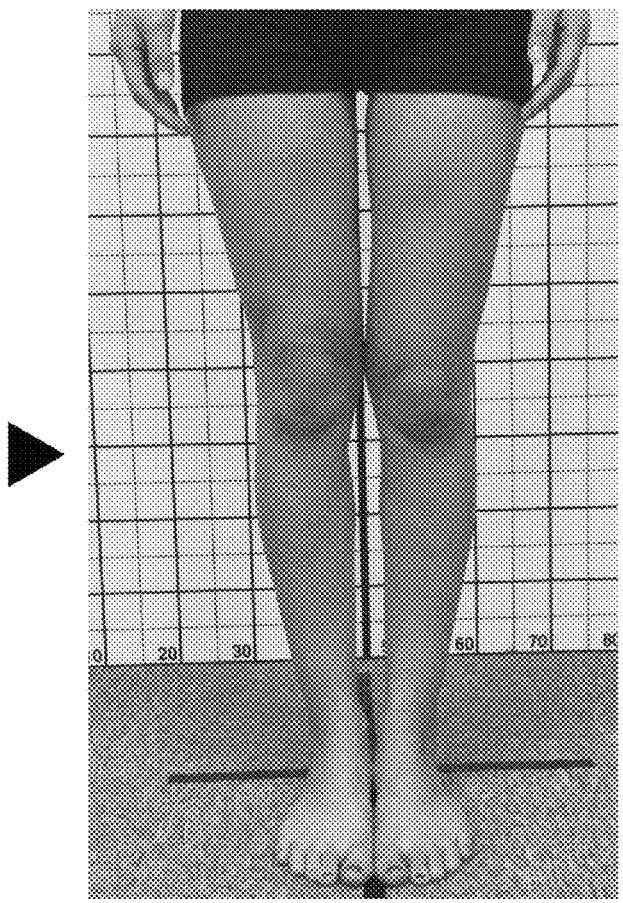
Figure 14:
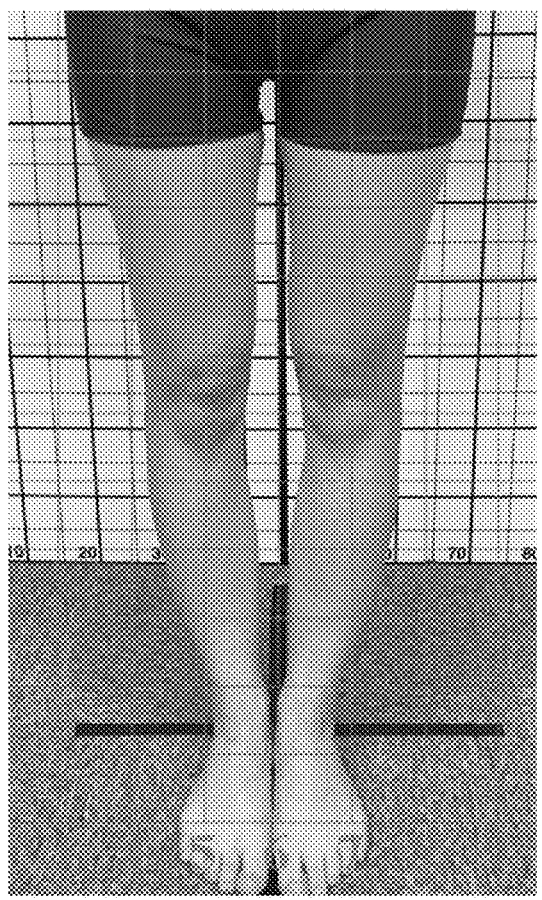
FIG. 14 is a view showing a measurement result of external appearance of legs of a subject in Test Example 2.
Figure 14:
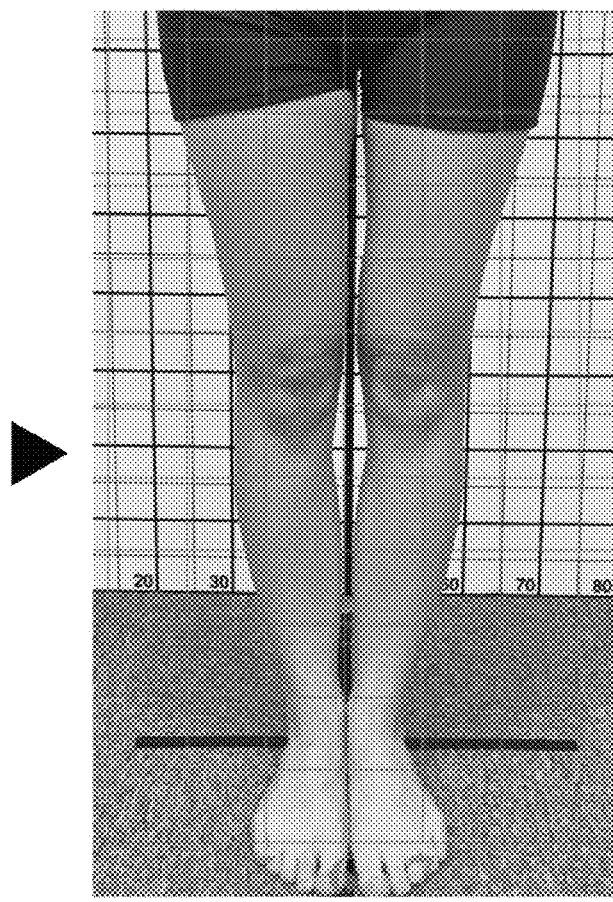

FIGS. 13 and 14 are views showing measurement results of external appearance of legs of the subject. As shown in FIGS. 13 and 14, it was confirmed that bow-legs and knock-knees of the subject were ameliorated as a result of the treatment according to the condition using the cosmetic device. Although FIGS. 13 and 14 are examples, amelioration of bow-legs and knock-knees were also confirmed on other subjects.

The present invention is widely applicable in a cosmetic field, a medical field, a hygienic field, and the like as a way to provide a cosmetic device that can be held with one hand and serve to dissolve cellulite and the like causing obesity and the like, providing high industrial applicability.

What is claimed is:

1. A cosmetic device comprising:
    a main body part provided with an insertion part formed by a space that can be inserted with a user's hand, and a placement part that can be placed with a palm of the user's hand inserted into the insertion part, on an outer surface;
    a roller disposed at an opening formed on a bottom surface of the main body part and capable of outputting a stimulation signal; and
    a suction pump contained in the main body part and configured to suck external air from the opening wherein a side of the main body part on which the user's hand is inserted is a bill shape in side view in which the insertion part is formed between an upper and lower bill portions, the placement part is an upper surface of the lower bill portion, and the main body part is formed with a finger insertion part that communicates with the insertion part and is formed by an opening hole that can be inserted with a finger of the user.

2. The cosmetic device according to claim 1, wherein the roller is made of a conductive material.

3. The cosmetic device according to claim 1, further comprising an air vent mechanism to discharge the sucked air to outside.

4. The cosmetic device according to claim 1, further comprising a drain tank that stores drain contained in the sucked air and is detachable from the main body part.

5. The cosmetic device according to claim 1, wherein the roller is attached to a roller cup detachable from the bottom surface of the main body part.

6. The cosmetic device according to claim 1, wherein
a lower surface of the upper bill portion and the upper surface of the lower bill portion are formed in a rounded shape convex upward, and
in a state where the user inserts a hand into the insertion part and a finger into the finger insertion part, the placement part fits in the palm.

7. The cosmetic device according to claim 2, wherein:
a lower surface of the upper bill portion and the upper surface of the lower bill portion are formed in a rounded shape convex upward, and
in a state where the user inserts a hand into the insertion part and a finger into the finger insertion part, the placement part fits in the palm.

8. The cosmetic device according to claim 2, further comprising an air vent mechanism to discharge the sucked air to outside.

9. The cosmetic device according to claim 2, further comprising a drain tank that stores drain contained in the sucked air and is detachable from the main body part.

10. The cosmetic device according to claim 2, wherein the roller is attached to a roller cup detachable from the bottom surface of the main body part.

\* \* \* \* \*